United States Patent [19]
Gavish

[11] Patent Number: 6,090,037
[45] Date of Patent: Jul. 18, 2000

[54] MODIFICATION OF BIORHYTHMIC ACTIVITY

[76] Inventor: Benjamin Gavish, 65 Yasmin Street, 90805 Mevasseret Zion, Israel

[21] Appl. No.: 09/101,540

[22] PCT Filed: Jan. 21, 1997

[86] PCT No.: PCT/IL97/00026

§ 371 Date: Oct. 3, 1998

§ 102(e) Date: Dec. 3, 1998

[87] PCT Pub. No.: WO97/26822

PCT Pub. Date: Jul. 31, 1997

[51] Int. Cl.[7] .............................. A61M 21/00; A61B 5/08
[52] U.S. Cl. .................................................. 600/27
[58] Field of Search .................. 600/26, 27, 28, 600/529, 534, 544, 545, 300; 607/207, 23–25

[56] References Cited

U.S. PATENT DOCUMENTS

| | | |
|---|---|---|
| 4,928,704 | 5/1990 | Hardt . |
| 5,076,281 | 12/1991 | Gavish . |
| 5,167,610 | 12/1992 | Kitado et al. .............................. 600/26 |
| 5,207,230 | 5/1993 | Bowers . |
| 5,267,942 | 12/1993 | Saperston ................................... 600/28 |
| 5,291,894 | 3/1994 | Nagy . |
| 5,295,490 | 3/1994 | Dodakian . |
| 5,343,871 | 9/1994 | Bittman et al. . |
| 5,365,939 | 11/1994 | Ochs . |
| 5,423,328 | 6/1995 | Gavish . |
| 5,709,217 | 1/1998 | Von Groningen ....................... 600/534 |
| 5,800,337 | 9/1998 | Gavish ..................................... 600/27 |

FOREIGN PATENT DOCUMENTS

| | | |
|---|---|---|
| 2042535 | 3/1972 | Germany . |
| 2713891 | 10/1978 | Germany . |
| 3406135 | 8/1985 | Germany . |
| 2035088 | 6/1980 | United Kingdom . |

*Primary Examiner*—Samuel G. Gilbert
*Attorney, Agent, or Firm*—Townsend and Townsend and Crew LLP

[57] ABSTRACT

A system for modifying naturally occurring biorhythmic activity including a monitor for analyzing biorhythmic activity of a user, a biorhythmic activity modifier for providing to the user a stimulus input which is operative to change at least one aspect of the biorhythmic activity of the user, and a driver operative to control the operation of the biorhythmic activity modifier, so as to change at least one non-frequency characteristic of the input to the user, in response to changes in the biorhythmic activity of the user during operation of the modifier. A method for modifying naturally occurring biorhythmic activity is also described.

18 Claims, 21 Drawing Sheets

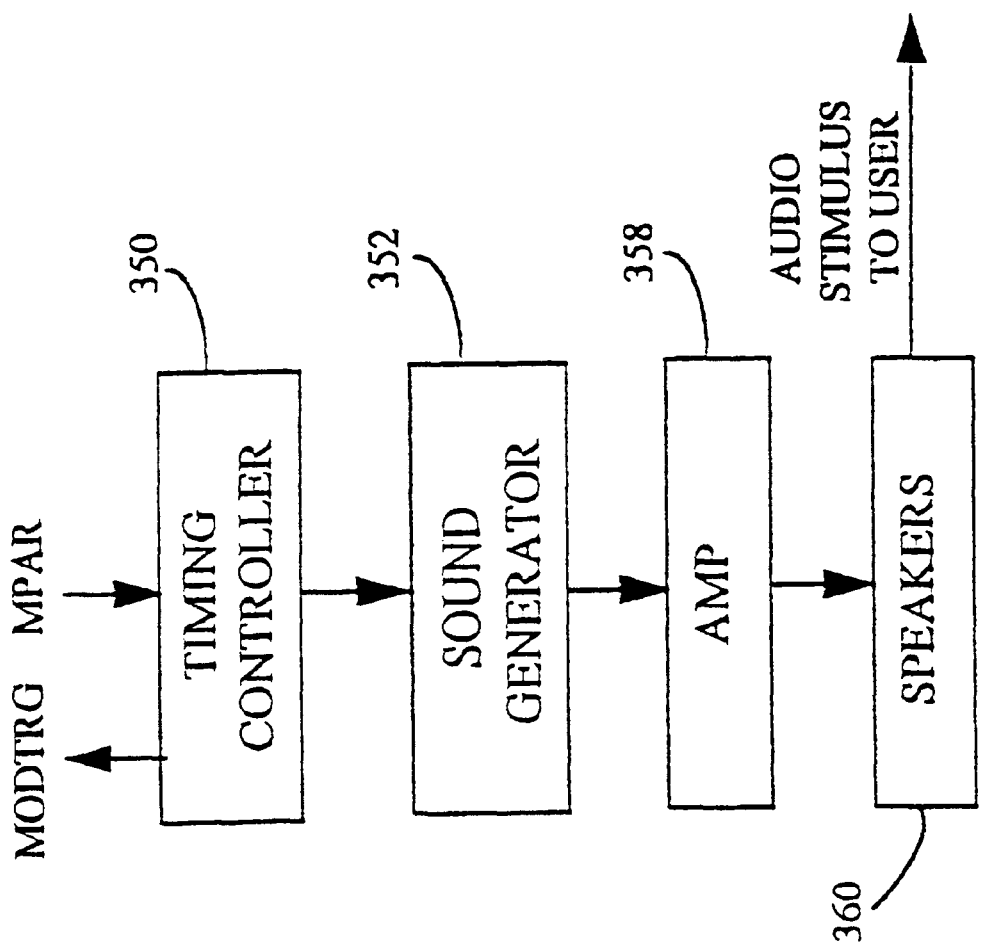

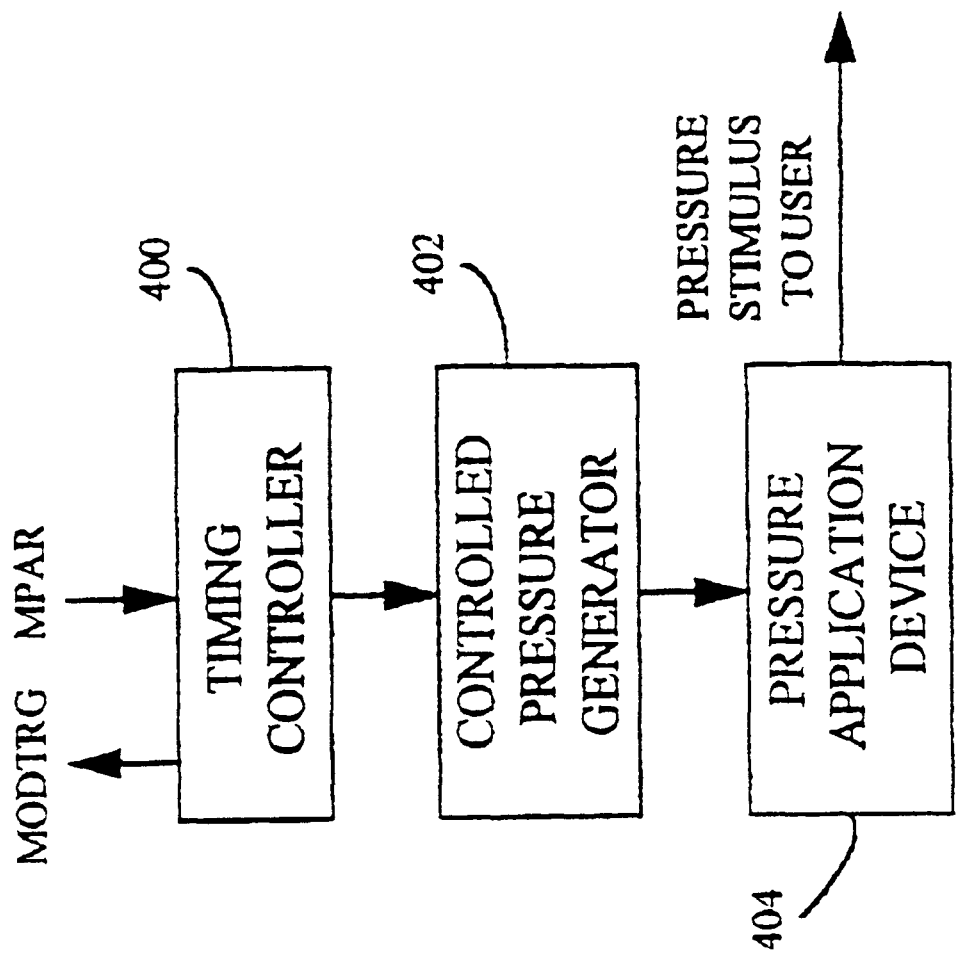

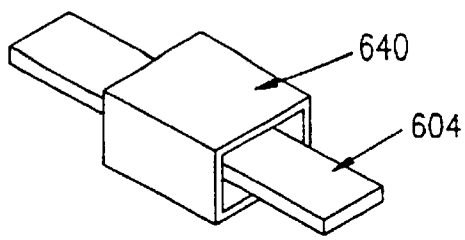
FIG. 17A
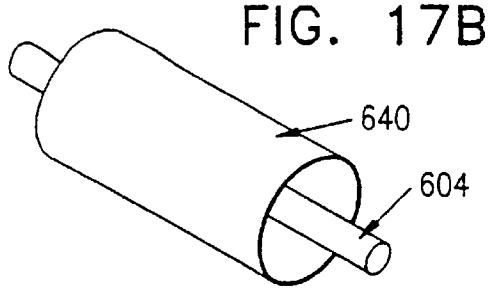
FIG. 17B
FIG. 17C
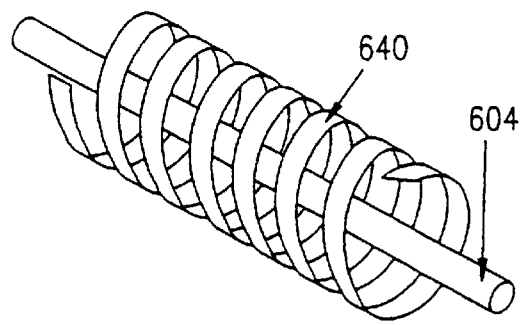
FIG. 18
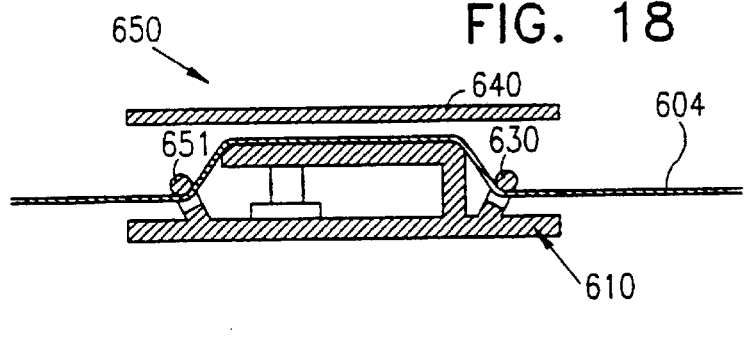
FIG. 19
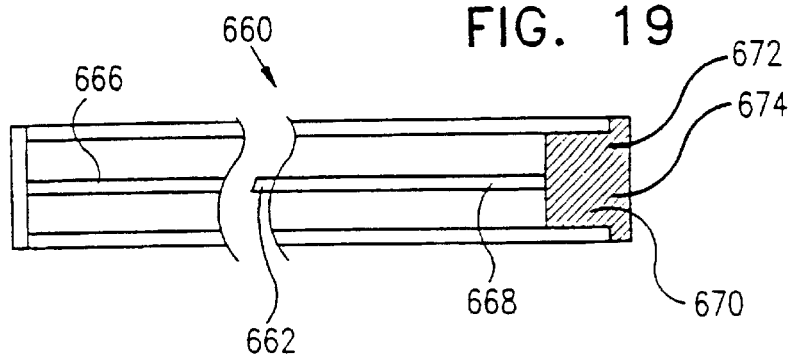

MODIFICATION OF BIORHYTHMIC ACTIVITY

FIELD OF THE INVENTION

The present invention relates to systems and methods for modification of biorhythmic activity.

BACKGROUND OF THE INVENTION

Various techniques and systems have been proposed for modification of biorhythmic activity. The following patents are believed to represent the state of the prior art: U.S. Pat. No. 5,267,942 to Saperston, entitled Method For Influencing Physiological Processes Through Physiologically Interactive Simuli. U.S. Pat. No. 5,076,281 to Gavish, the present inventor, entitled Device and Method for Effecting Rhythmic Body Activity. Further relevant prior art appears in the References Cited listings of the aforesaid patents and in the Background sections thereof. U.S. Pat. No. 5,423,328 also to Gavish describes a monitoring device which is particularly suitable for use in the present invention. The disclosures of all of these patents are hereby incorporated by reference.

SUMMARY OF THE INVENTION

The present invention seeks to provide an improvement to the systems and techniques of the prior art.

There is thus provided in accordance with a preferred embodiment of the present invention a system for modifying naturally occurring biorhythmic activity including a monitor for analyzing biorhythmic activity of a user, a biorhythmic activity modifier for providing to the user a stimulus input which is operative to change at least one aspect of the biorhythmic activity of the user, and a driver operative to control the operation of the biorhythmic activity modifier, so as to change at least one non-frequency characteristic of the input to the user, in response to changes in the biorhythmic activity of the user during operation of the modifier.

Preferably, the driver is operative to change at least one non-frequency characteristic of the input to the user in response to at least one corresponding change in a non-frequency characteristic of the biorhythmic activity of the user during operation of the modifier.

In accordance with a preferred embodiment of the present invention the non-frequency characteristic of the input to the user forms part of a recurrent pattern.

Preferably, the driver is also responsive to selectable operator commands for governing the manner in which the non-frequency characteristic of the input to the user is changed.

In accordance with a preferred embodiment of the present invention the non-frequency characteristic includes the relationship of at least two components of a generally recurrent pattern.

Preferably the selectable operator commands are operative to select at least one of a plurality of relationships between at least two characteristics of a generally recurrent pattern of the input to the user which are modified.

In accordance with a preferred embodiment of the present invention the modifier is also responsive to the time relationship between a generally recurrent pattern in the biorhythmic activity of the user and a generally recurrent pattern in the input to the user.

Preferably, the driver is operative in an at least partially predetermined manner.

In accordance with a preferred embodiment of the present invention the system also comprises a shift detector receiving inputs from the monitor and the modifier and providing a shift correction output to the modifier.

Preferably, the shift detector also receives an input from the driver and is responsive thereto for providing the shift correction output to the modifier.

In accordance with a preferred embodiment of the present invention the input from the driver includes operator command determined instructions.

Preferably, the shift correction output is provided in response to the time relationship between the onsets of biorhythmic activity signals and stimulus inputs to the user.

In accordance with a preferred embodiment of the present invention the shift correction output is provided by delaying the onset of stimulus inputs to the user.

Preferably the shift correction output is provided by moving up the onset of stimulus inputs to the user.

In accordance with a preferred embodiment of the present invention the at least one non-frequency characteristic of the biorhythmic activity of the user forms part of a recurrent pattern.

The stimulus input may be an audio input, a visual input, a tactile input or a combination of them.

Preferably, the monitor is operative to analyze respiration information.

There is additionally provided in accordance with a preferred embodiment of the present invention a method for modifying naturally occurring biorhythmic activity including analyzing biorhythmic activity of a user, providing to the user a stimulus input which is operative to change at least one aspect of the biorhythmic activity of the user; and changing at least one non-frequency characteristic of the input to the user, in response to changes in the biorhythmic activity of the user during operation of the modifier.

It is appreciated that the various stimulus inputs may be provided to a user individually or simultaneously in multiple forms. Thus for example, an audio stimulus may be combined with a visual and/or tactile stimulus, or two or more audio, visual or tactile stimuli may be provided simultaneously alone or together with other types of stimuli. For example, the audio stimulus may be provided in stereo form and the visual stimulus may be provided in stereo form in order to provide the user with three-dimensional perception of the stimulus.

BRIEF DESCRIPTION OF THE DRAWINGS

The present invention will be understood and appreciated more fully from the following detailed description, taken in conjunction with the drawings in which:

FIGS. 9A, 9B & 9C are block diagrams illustrating the three alternative embodiments of the structure of a pattern generator employed in an audio stimulus generating version of the system of FIG. 1 whose operation is illustrated generally in FIG. 4;

FIGS. 11A and 11B are block diagrams illustrating two alternative embodiments of a pattern generator employed in a pressure stimulus generating version of the system of FIG. 1 whose operation is illustrated generally in FIG. 4;

FIGS. 17A, 17B and 17C are simplified illustrations of a portion of the biorhythmic activity monitoring device of FIGS. 15, 16A and 16B, showing a stretchable belt disposed in a belt protector, constructed and operative in accordance with a preferred embodiment of the present invention;

FIG. 18 is a simplified sectional illustration of a portion of a biorhythmic activity sensor, constructed and operative in accordance with another preferred embodiment of the present invention; and FIG. 19 is a simplified sectional illustration of a portion of a biorhythmic activity sensor, constructed and operative in accordance with yet another preferred embodiment of the present invention.

DETAILED DESCRIPTION OF PREFERRED EMBODIMENTS

Figure 1:
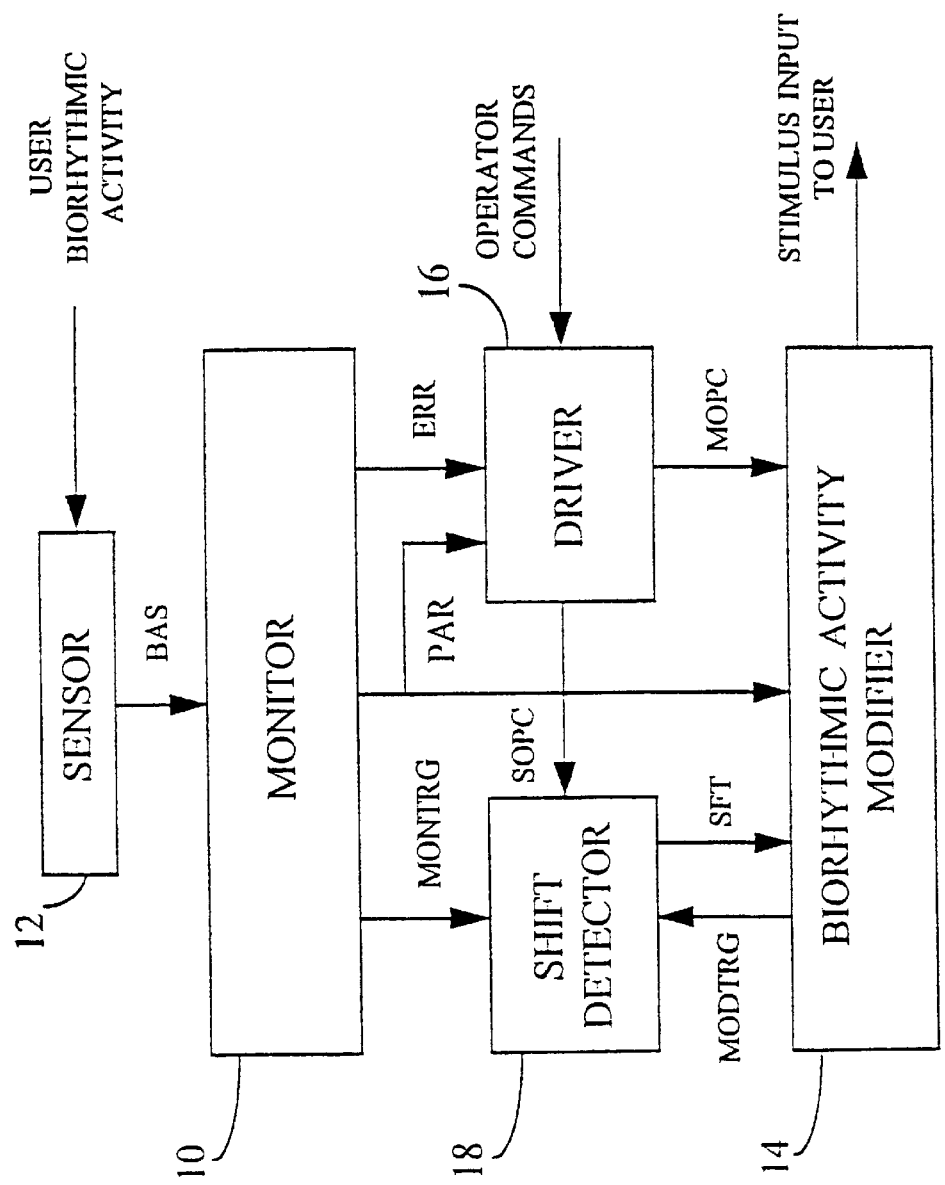
FIG. 1 is a simplified block diagram illustration of a system for modification of biorhythmic activity constructed and operative in accordance with a preferred embodiment of the present invention.

Reference is now made to FIG. 1, which is a simplified block diagram illustration of a system for modification of biorhythmic activity constructed and operative in accordance with a preferred embodiment of the present invention. The system of FIG. 1 preferably comprises a monitor 10 for analyzing biorhythmic activity of a user. Monitor 10 receives electrical signals representing biorhythmic activity of an individual, here designated BAS, from a biorhythmic activity sensor 12. A preferred biorhythmic activity sensor is that described and claimed in U.S. Pat. No. 5,423,328 to the present inventor, it being appreciated that any other suitable sensor may be employed alternatively or additionally. The connection to sensor 12 may be wired or wireless.

The operation of monitor 10 is principally to provide output indications representing one or more pattern components of the sensed biorhythmic activity of the user. Preferably, the output indications include parameter indications PAR which are of a quantitative nature and a MONTRG trigger indication which represents the timing of the biorhythmic pattern components. The monitor 10 also preferably provides an error indication ERR when it does not receive acceptable electrical signals representing biorhythmic activity of the user and thus cannot provide suitable parameter and trigger indications.

A biorhythmic activity modifier 14 receives the parameter indications from monitor 10 and is operative for providing to the user a stimulus input which is operative to change at least one aspect of the biorhythmic activity of the user. A driver 16 preferably but not necessarily also receives the parameter and error indications PAR and ERR from the monitor and is operative by an operator, who may be different from the user, to control the operation of the biorhythmic activity modifier 14 by providing a set of operational command inputs, collectively referred to as MOPC, so as to cause at least one non-frequency pattern component of the input to the user to be related to at least one non-frequency pattern component of the existing biorhythmic activity of the user which is sensed by sensor 12.

In accordance with a preferred embodiment of the invention, the driver 16 is responsive to operator commands, which may come from the user.

In accordance with one preferred embodiment of the invention, the modifier 14 may also be responsive to an output from a shift detector 18. Shift detector 18 preferably receives the MONTRG trigger indication from the monitor 10 as well as an MODTRG trigger indication from modifier 14 indicating the timing of the input to the user. The shift detector 18 is operative to measure the timing relationship between the two trigger indications MONTRG and MODTRG and to provide a timing shift indication SFT to the biorhythmic activity modifier 14 causing it to reduce the time separation between successive MONTRG and MODTRG trigger indications. The shift detector 18 receives an operational command input SOPC from driver 16 which governs the criteria according to which the shift detector 18 provides the timing shift indication SFT to the biorhythmic activity modifier 14.

The MOPC inputs supplied by driver 16 to biorhythmic activity modifier 14 govern the criteria according to which the modifier 14 responds to the PAR and SFT indications received thereby.

Figure 2:
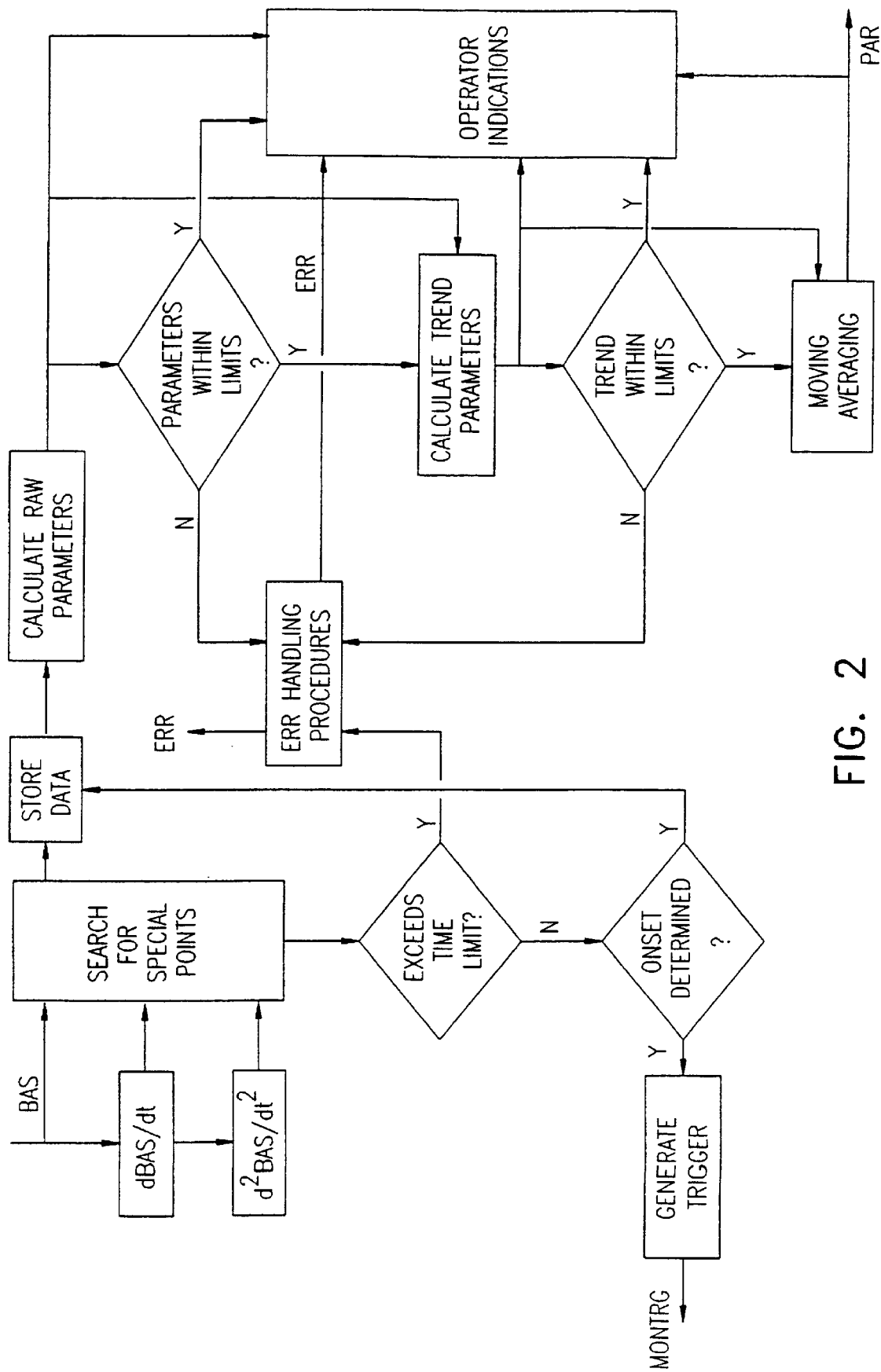
FIG. 2 is a flowchart illustrating operation of a monitor employed in the system of FIG. 1.

Reference is now made to FIG. 2, which is a flowchart illustrating operation of a monitor employed in the system of FIG. 1. The BAS signals received from biorhythmic activity sensor 12 are subjected to pattern and trend analysis. The pattern analysis preferably includes pattern identification which constitutes identification of recurrent features in the signals, such as rising and falling parts of the signals and expresses these features in parameters which are associated with identifiable components of the physiological activity monitored by sensor 12. The trend analysis constitutes identification of changes in one or more parameters in the recurrent features, such as a decrease in amplitude over multiple signal patterns.

A description of prior art pattern and trend analysis is provided in U.S. Pat. No. 5,076,281 of the present inventor, the disclosure of which is hereby incorporated by reference. The pattern and trend analysis employed in the present invention goes beyond that described in U.S. Pat. No. 5,076,281 as will now be described with additional reference to FIG. 6.

Figure 6:
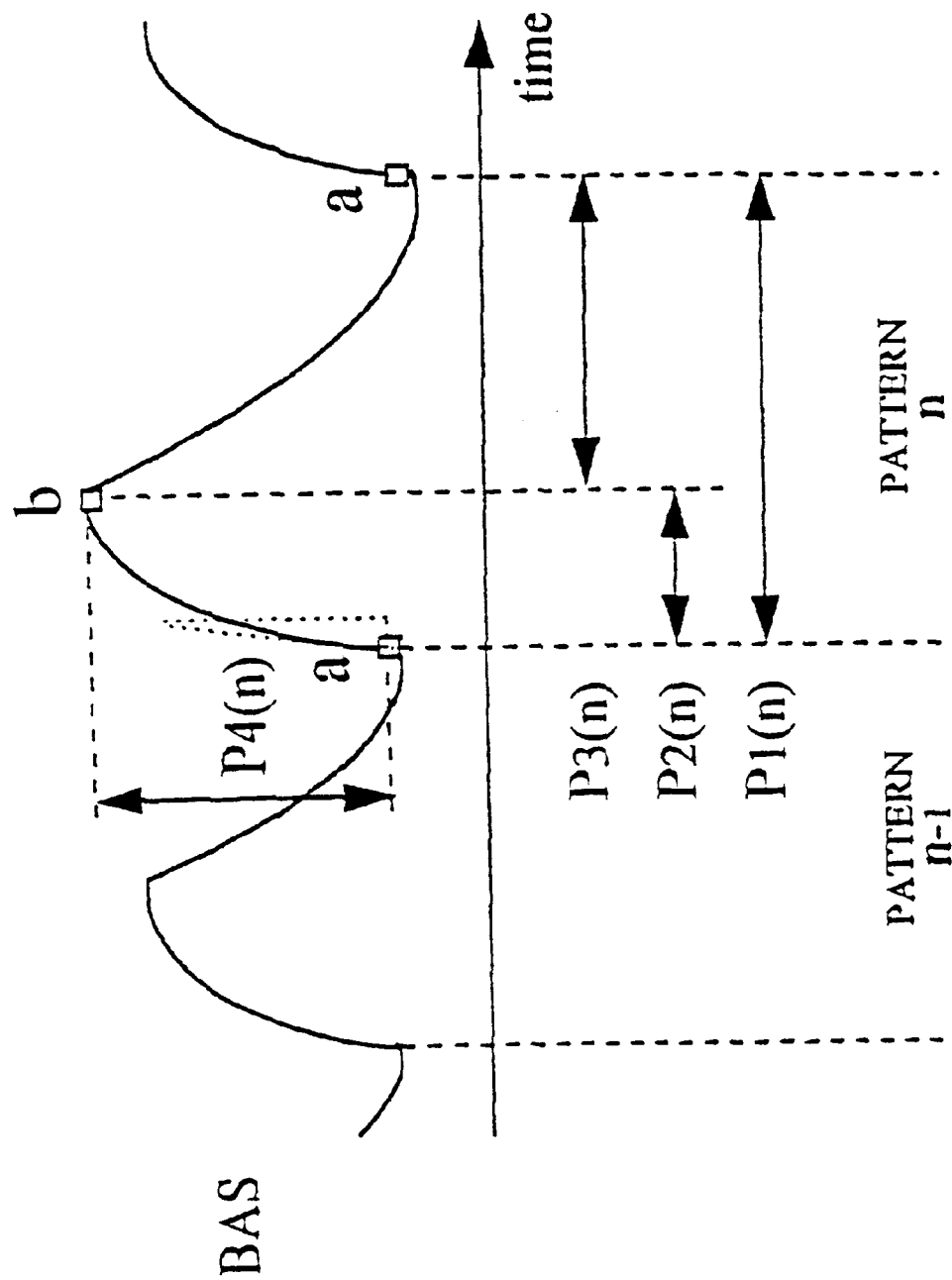
FIG. 6 is an annotated illustration of a typical monitored biorhythmic activity signal which is subject to analysis in accordance with the present invention.

FIG. 6 illustrates a typical respiration signal as sensed by a belt-type respiration sensor as described in U.S. Pat. No. 5,423,328. The BAS signals and their changes thereof with respect to time changes, are operated upon by a subroutine which provides a search for special points. In general these special points are located where the BAS signal or the first and second time derivatives thereof reach minima, maxima and zero. Typical special points in the signal shown in FIG. 6 are a, at which the first time derivative has a maximum following a local minimum; and b, at which the BAS signal reaches a maximum, the first time derivative is at zero and the second time derivative is negative.

In accordance with a preferred embodiment of the present invention, most or all of the special points are detected in real time. The remainder of the BAS signal may be analyzed in real time or stored for near-real time analysis.

Following determination of the locations of the special points, a time relationship analysis is performed to determine whether the time separation between special points exceeds predetermined limits. The time relationship analysis is preferably carried out on predetermined special points. The special points subject to the time relationship analysis may or may not be mutually adjacent. If the limits are exceeded an output is provided which initiates error handling procedures.

If the limit is not exceeded, it is necessary to determine if the special point is an onset point. If this point is determined to be an onset point, the onset of a signal pattern has been detected. Although it is appreciated that the onset may be arbitrarily determined, depending on the nature of the signal, any one of the special points which appears distinctiveness in the signal environment may be selected. In the present description, a is referred to as indicating onset of a signal pattern.

Once the signal onset is determined, the MONTRG signal output of the monitor 10 (FIG. 1) is provided to shift detector 18 (FIG. 1). Information relating to the special points, including their location relative to the onset of the pattern and other special points, are stored.

The stored special points are then used to calculate raw parameters which are eventually employed to provide the PAR outputs of the monitor 10 (FIG. 1). Examples of raw parameters in a BAS pattern having one rising part and one falling part include the following (FIG. 6):

P1(n) Pattern duration—the time between successive pattern onsets, which is the sum of P2(n)+P3(n) defined hereinbelow, n indicating the number of the pattern;

P2(n) Pattern rise time—the time separation between point a and the following point b, n indicating the number of the pattern;

P3(n) Pattern fall time—the time separation between point b and the following point a, n indicating the number of the pattern;

P4(n) Pattern maximum amplitude—the signal amplitude at point b measured with reference to previous point a. It is appreciated that additional parameters may include relationships between the above-mentioned parameters as well as any other suitable parameters.

As illustrated in FIG. 2, at every stage of the operation, the different parameters, for example the raw parameters, may be displayed to the operator as operator indications, thereby allowing the operator to control all steps of the operation.

The raw parameters are also examined for acceptability to see whether they fit within predetermined limits. If not, an output is provided which initiates error handling procedures, which may provide to the operator an error output indication ERR.

If the parameters fit within the predetermined limits, trend parameters are then calculated. Trend parameters indicate the changes in each of the raw parameters and their mutual relationships over time in a series of acceptable patterns. Examples of trend parameters include changes in the absolute or relative value of a parameter between successive patterns.

The trend parameters are then examined for acceptability to see whether they fit within predetermined limits. If not, an output is provided which initiates error handling procedures, which may provide an error output indication at an operator interface. Error indications are typically provided in the case of irregularity in the raw parameters or sudden sharp changes therein.

So long as the raw and trend parameters fit within the predetermined limits and are thus acceptable they are subject to moving averaging over a predetermined number of patterns. These moving averages are supplied to the modifier 14 and driver 16 as the PAR inputs (FIG. 1).

Indications of the raw and trend parameters which fall within the predetermined limits of acceptability and error indications ERR and the moving averages of those parameters may also be supplied to the operator.

Figure 3:
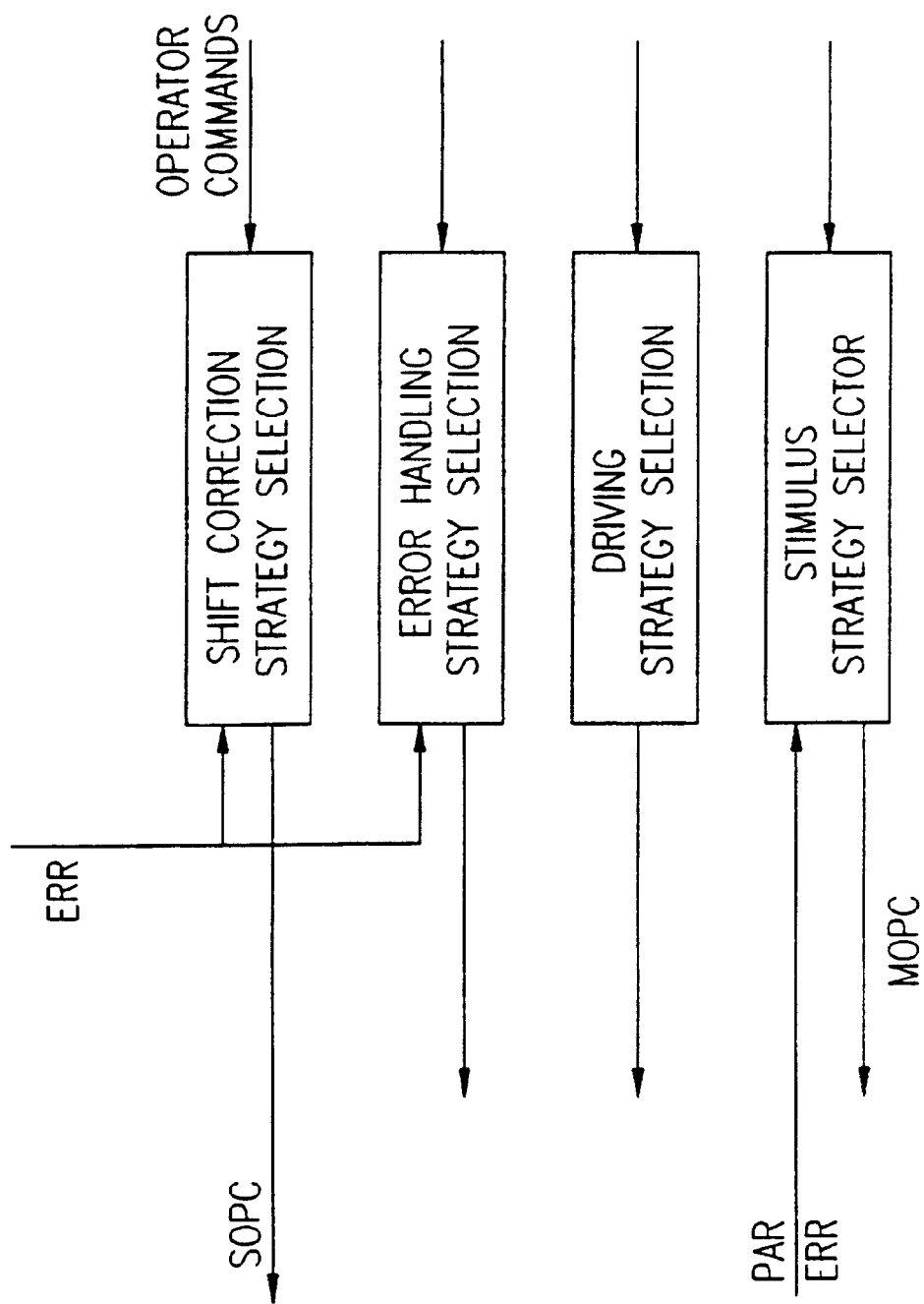
FIG. 3 is a flowchart illustrating operation of a driver employed in the system of FIG. 1.

Reference is now made to FIG. 3, which is a flowchart illustrating operation of a driver, such as driver 16, employed in the system of FIG. 1. The driver is responsive to operator commands to provide a plurality of functionalities which will now be described:

Shift correction strategy—This determines the manner in which shift correction is effected. Shift correction relates to the time difference between the onset of each pattern in the BAS signal which is monitored and the onset of each corresponding pattern in the stimulus output provided by modifier 14 (FIG. 1). The mechanism of shift correction will be described hereinbelow in greater detail with reference to FIG. 8.

It is noted that when an ERR output is present, indicating an irregular BAS signal, shift correction is normally not carried out. Typical matters dealt with by the shift correction strategy are the time relationship or the number of elapsed patterns between successive corrections and the magnitude of shifts that are effected.

Error handling strategy—This determines the manner in which an output indication of error is provided to the operator, e.g. in a visual, audio, tactile or other suitable manner.

Driving strategy—This determines which parameters are to be modified, to what degree and in what manner.

Stimulus strategy—This determines the general and specific type or types of stimulus that are employed. For example, when audio stimuli are employed, the nature of a sound pattern and even the identity of a musical composition and its internal structure, as well as its instrumentation, spectral distribution and amplitude may be selected. As another example, when visual stimuli are employed, the shape, color, dynamics, intensity and complexity of the visual stimulus may be selected.

The stimulus strategy may also include determination of any of the foregoing features based directly or indirectly on the characteristics of the monitored BAS signal in real time or near real time, responsive to the ERR and PAR signal outputs of the monitor 10 (FIG. 1).

One or more types of stimulus and the balance between them may also be selected. An independently controlled pattern generating metronome stimulus may also be selected by the operator.

The driver 16 provides modifier operational commands (MOPC), embodying all of the above strategy selections, to the modifier 14.

Figure 4:
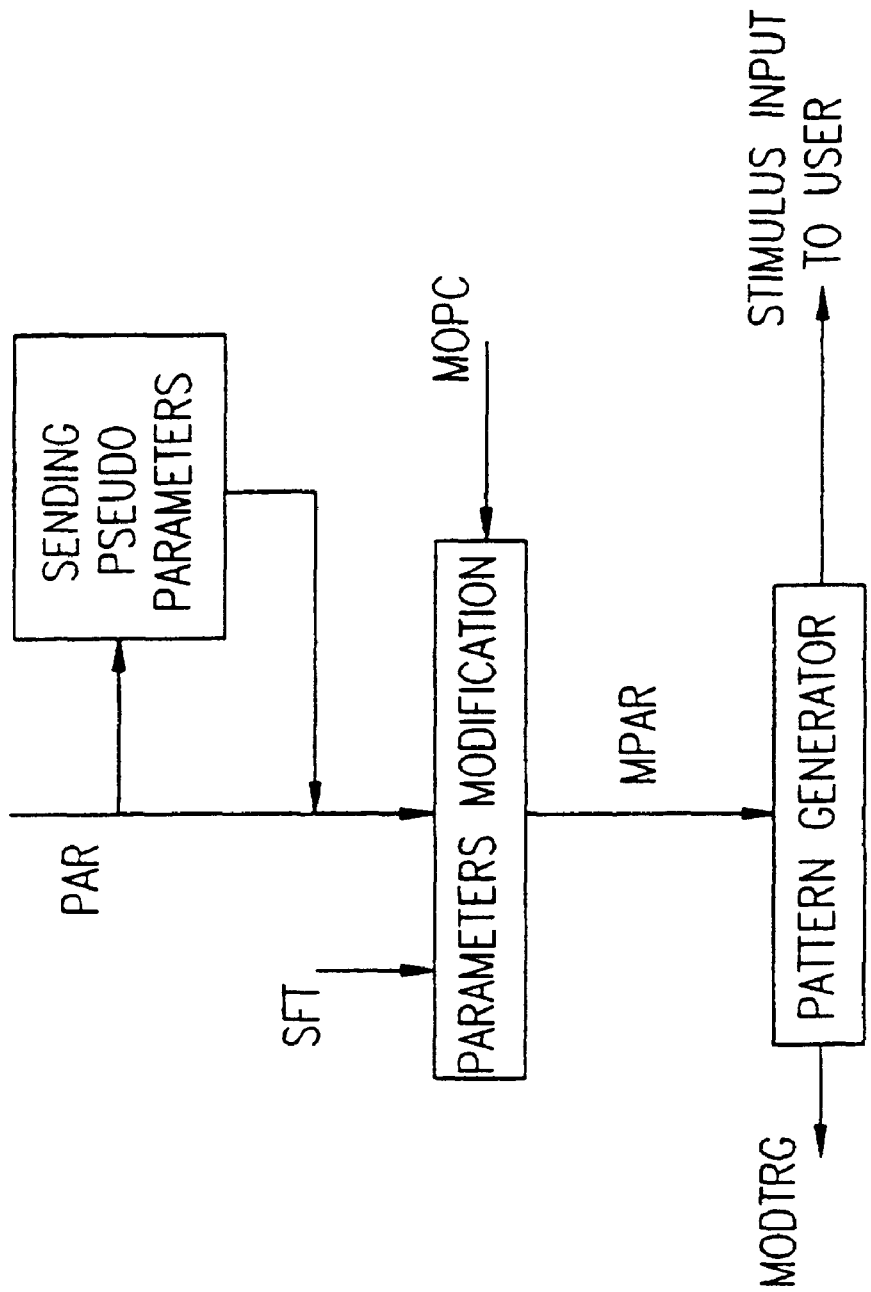
FIG. 4 is a flowchart illustrating operation of a biorhythmic activity modifier employed in the system of FIG. 1.

Reference is now made to FIG. 4, which is a flowchart illustrating operation of the modifier 14 employed in the system of FIG. 1. The modifier 14 receives PAR signals from the monitor 10. In the absence of such signals, pseudo-PAR signals are generated. In the preferred embodiment of the present invention, the pseudo-PAR signals are identical to the last received PAR signals.

The PAR signals and the pseudo-PAR signals, to the extent that each are present, are modified to produce modified-PAR (MPAR) signals in accordance with criteria represented by the MOPC inputs received from the driver 16, in accordance with the strategies selected by the operator and in accordance with the SFT input from shift detector 18. The MPAR signals are employed to generate patterns of stimulus inputs to a user.

Simultaneously with generation of the patterns of stimulus inputs to a user, the modifier 14 provides a MODTRG trigger output to shift detector 18, which indicates the onset of each pattern of the stimulus inputs to the user.

Figure 5:
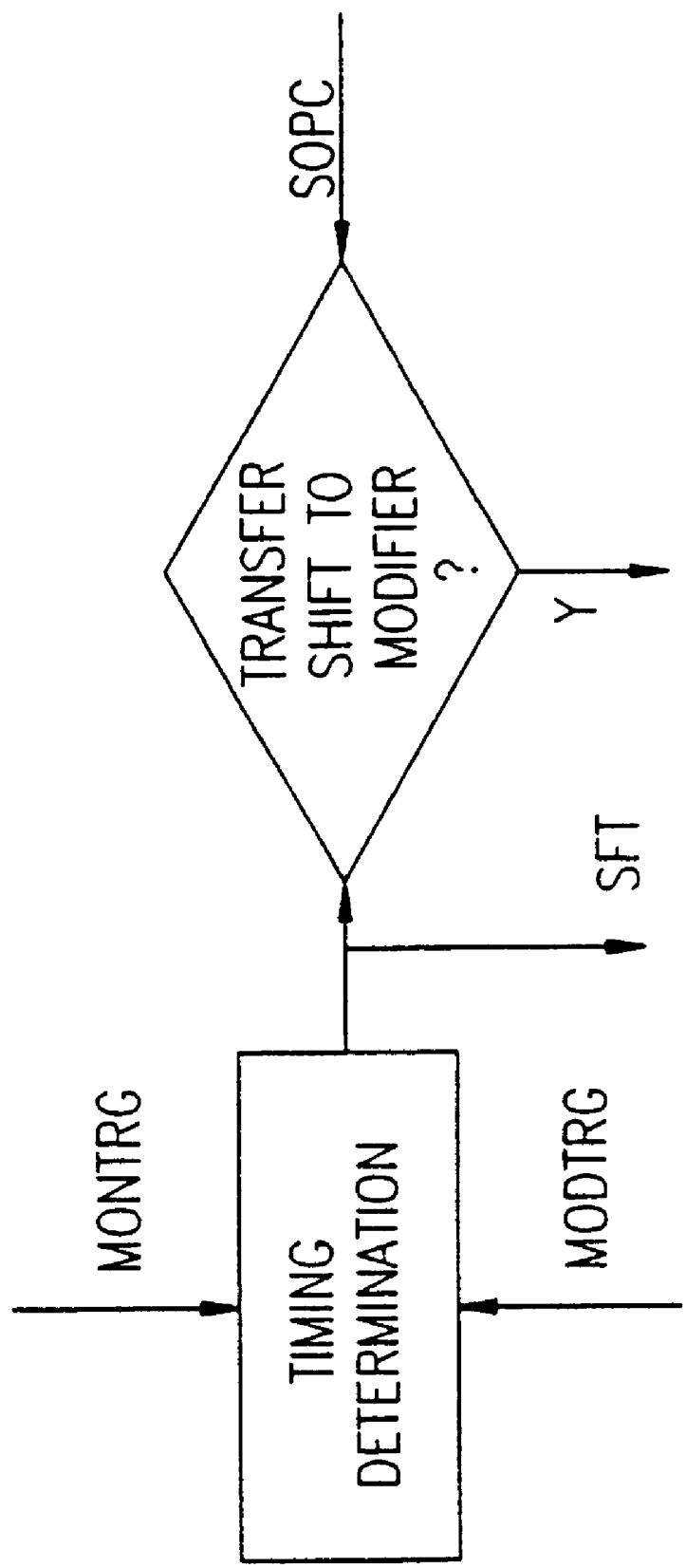
FIG. 5 is a flowchart illustrating operation of a shift detector employed in the system of FIG. 1.

Reference is now made to FIG. 5 which illustrates operation of the shift detector 18 of the apparatus of FIG. 1. The shift detector 18 receives both the MODTRG signal from the modifier 14, giving the onset of the stimulus output patterns and the MONTRG output from the monitor 10, giving the onset of the monitored BAS signal. The shift detector 18 determines the time interval between the pattern onsets represented by these two inputs, which may arrive at the shift detector 18 in different order and provides an output indication SFT indicating whether the stimulus output onsets trail the BAS signal onsets and if so, by how much.

If the stimulus output onsets trail the BAS signal onsets by more than a predetermined time, as indicated by the SFT output indication, the shift detector enables the SFT input to the modifier 14, which input is also determined by the SOPC input received from the driver 16 in accordance with the selected shift correction strategy. The SFT input causes the modifier 16 to shift the onsets of the stimulus output patterns so as to minimize the amount by which the stimulus output onsets trail the BAS signal onsets. It is appreciated that depending on the amount by which the stimulus output onsets trail the BAS signal onsets and the stability of the BAS signal, the entire required correction may not be made immediately.

Figure 7:
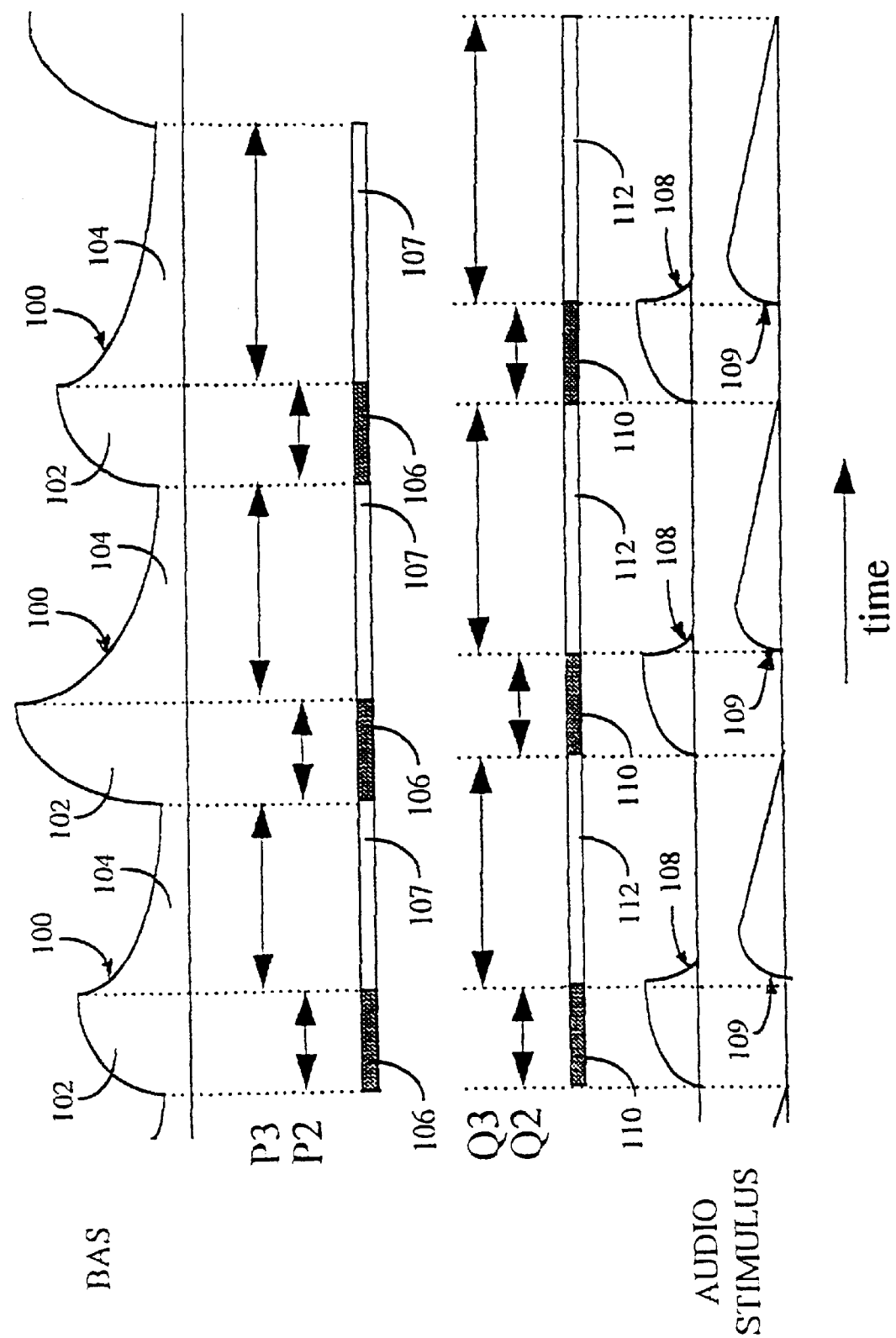
FIG. 7 is an illustration of modification of a typical monitored biorhythmic activity signal in accordance with the present invention which illustration ignores time shifts and the correction thereof.

Reference is now made FIG. 7, which is an illustration of modification of a typical monitored biorhythmic activity signal in accordance with the present invention. For the purposes of clarity and simplicity of explanation, the illustration of FIG. 7 and the explanation thereof which follows ignores time shifts and the correction thereof, which are explained hereinbelow with reference to FIG. 8.

FIG. 7 includes an illustration of a typical BAS signal 100 which is received by monitor 10 (FIG. 1). In the present example, the BAS signal may represent a respiration signal produced by a sensor of the type described in U.S. Pat. No. 5,423,328, it being appreciated that alternatively, depending on the type of sensor employed, the BAS signal may be any suitable signal representative of biorhythmic activity of interest.

The BAS signal 100 may be seen to be composed of two parts, an inspiration part 102, which is the rising part of the signal, and an expiration part 104, which is the falling part of the signal. The durations of the inspiration part 102 and expiration part 104 are indicated by respective shaded and unshaded portions 106 and 107. The relationship between the inspiration part 102 and the expiration part 104 and the parameters P2 and P3 are indicated, P2 representing the inspiration part, whose duration is indicated by reference numeral 106 and P3 representing the expiration part, whose duration is indicated by reference numeral 107.

For some applications, as inducing relaxation, it is desired to increase P3. This is preferably accomplished without a corresponding increase in P2, thereby increasing the ratio of P3 to P2. In some other applications, as in fitness, a decrease of P2 may be preferable. In practice, where an audio stimulus is provided to the user, a first audio sound, represented by a waveform 108, such as a trumpet sound, represents the desired inspiration part and a second audio sound, represented by a waveform 109, such as a flute sound, represents the desired expiration part. The sound intensity is represented by the amplitude of waveforms 108 and 109.

With each successive pattern, the duration of the flute sound increases relative to the duration of the trumpet sound, thus causing the user to gradually increase the duration of the expiration part of his respiration both in the absolute and relative to the duration of the inspiration part of his respiration.

In FIG. 7, the duration of that part of the audio stimulus input to the user which is identified by the user with inspiration is identified as Q2, while the duration of that part of the stimulus input to the user which is identified by the user with expiration is identified as Q3. Q2 is identified by shaded portion 110, while Q3 is identified by unshaded portion 112. It is seen that the ratio of Q3 to Q2 increases gradually with each successive pattern.

In the preferred embodiment illustrated in FIG. 7, Q2 of the audio stimulus, which indicates the duration 110, is intended to overlay the inspiration portion 102 of the BAS. Q2 is equal to <P2>, which is the moving average of P2, and corresponds to a preferred strategy, supplied by the MOPC, of not changing the duration 106 of the inspiration portion 102 of the user. On the other hand, Q3 of the audio stimulus, which indicates the duration 112, is selected to be longer than the expiration portion 104 of the user. Q3 is longer than <P3>, the moving average of the expiration duration 107 of the user, by about 0.5 to 1 second.

It is appreciated that as distinguished from the prior art, which merely changes the parameter P1, which is the duration of the entire pattern, the present invention changes the relative durations of portions of the pattern. While this may have the effect of changing the duration of the entire pattern and thus changing the frequency of the biorhythmic signal, the present invention is nevertheless concerned principally with changing the both the absolute and relative durations of portions of the pattern independently of changes in the frequency of the biorhythmic signal. Alternatively or additionally, the present invention also provides chances in other non-frequency parameters, such as the relative amplitudes of various parts of a pattern, which may include two or more parts.

As noted above, FIG. 7 does not deal with time shifts or the correction thereof. In accordance with a preferred embodiment of the invention, and as distinguished from the prior art, the present invention corrects for time shifts, which otherwise would render the modifications described in FIG. 7 largely useless.

It is appreciated by the present inventor, in contrast to the teaching of the prior art, that in order for entraining to occur, the stimuli must be coextensive in time with the biorhythmic signal parts that they are intended to stimulate. In order to enhance the user-perceived synchronization between the stimuli and the corresponding biorhythmic signal parts, time shift correction is required.

The present inventor has realized that the temporal nature of the entrainment phenomenon requires that modifications to the stimulus applied to the user occur in the time domain rather than in the frequency domain. Modifications in the time and frequency domains are not equivalent to each other or mutually reciprocal when generally recurrent, but not identical, patterns are concerned.

This can be demonstrated by calculating the breathing rate indicated by a sequence of breaths of duration Ti=4, 4.8, 6, 3.2 and 2 seconds.

In the time domain, the respiration rate is expressed in units of breaths per minute by $60/<Ti>$, where $<Ti>$ is the average breath duration which equals:

(4+4.8+6+3.2+2)/5 seconds=4 seconds.

Thus the respiration rate is given as 15 breaths per minute.

In the frequency domain, the respiration rate is equal to the average of the individual respiration rates, expressed as $<60/Ti>$, and here equals:

(60/4+60/4.8+60/6+60/3.2+60/2)/5=17.25 breaths per minute.

It is seen that the results of the two calculations differ by 15% in this case.

In general $<1/Ti>$ is not equal to $1/<Ti>$ because shorter durations dominate in $<1/Ti>$, while longer durations dominate in $1/<Ti>$.

Time shifts between the biorhythmic signals and the stimulus input occur for the following reasons:

1. Variation in the periodicity of the biorhythmic signals from pattern to pattern is well established but cannot be predicted in advance for each individual pattern. Furthermore, the periodicity of the biorhythmic signals is affected by the stimuli during application of the stimulus input. Thus, the stimulus input cannot be timed in advance such that the onset of each part thereof corresponds precisely to the onset of each individual pattern of the biorhythmic signal.

2. The timing of the stimuli in the stimulus inputs is based on averages of past timing of monitored biorhythmic signals due to physiological reasons. The user requires a relatively regular and predictable stimulus in order for successful entrainment to take place. These conditions are generally not fulfilled in the prior art.

Figure 8:
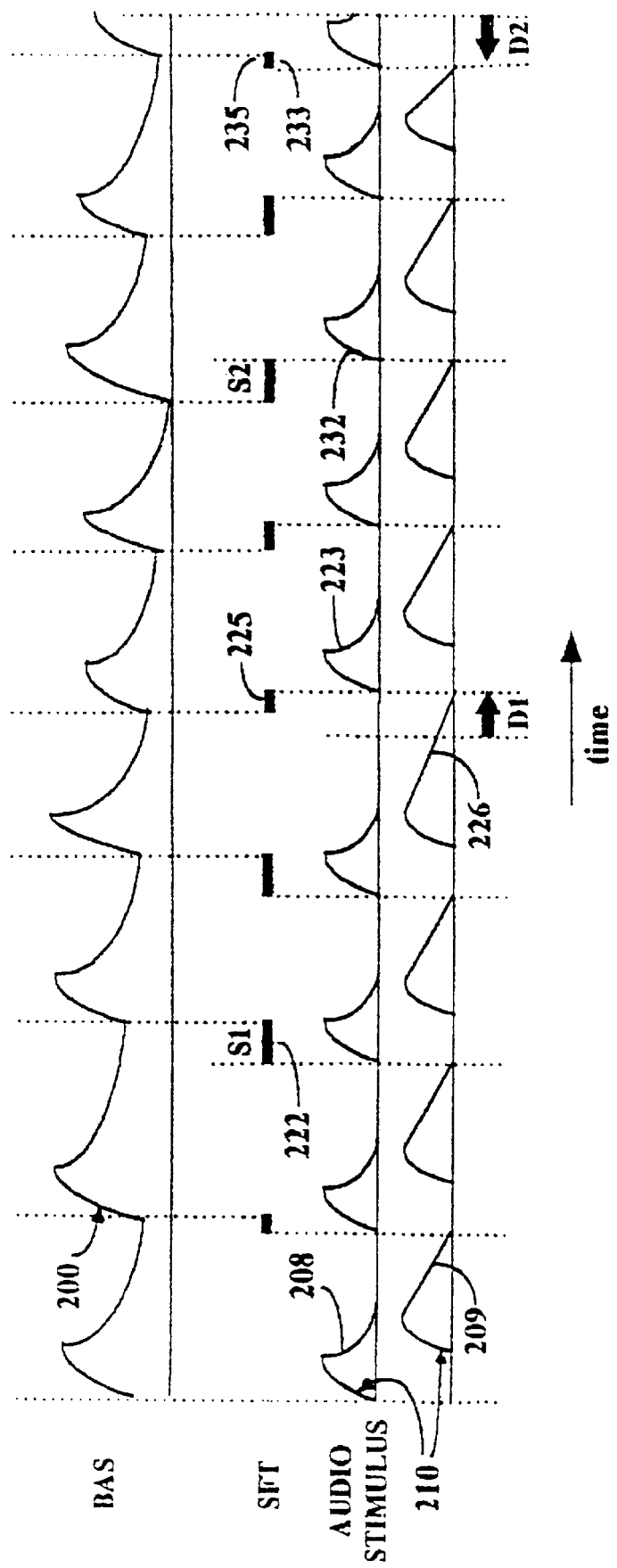
FIG. 8 is an illustration of shift correcting modification of a typical monitored biorhythmic activity signal in accordance with the present invention.

Reference is now made to FIG. 8 which is an illustration of shift correcting modification of a typical monitored biorhythmic activity signal in accordance with the present invention.

FIG. 8 includes an illustration of a typical BAS signal 200 which is received by monitor 10 (FIG. 1) and may be identical to the BAS signal 100 illustrated in FIG. 7. FIG. 8 also includes an illustration of a typical audio stimulus 210 comprising two sound stimulus inputs 208 and 209 to the user, which may be identical to stimulus inputs 108 and 109 respectively, shown in FIG. 7. For the reasons seen above, following one or more patterns, the onsets of the BAS signal 200 and the stimulus input 208 may not coincide, as indicated at reference numeral 222, where the onset of the stimulus input lags behind the onset of the BAS signal by a time duration S1.

In order to compensate for this lag, the present invention causes the onset of a following stimulus input pattern, indicated by reference numeral 223 to be delayed by an amount D1 which may be equal to S1 or be a suitably weighted amount dependent on S1, so as to reduce or eliminate the amount of lag, as seen at reference numeral 225. The delay D1 in onset is seen to be achieved preferably by extending the expiration influencing part of the stimulus signal, here indicated by reference numeral 226. Alternatively, the delay in onset may be effected by increasing the duration of the inspiration influencing part or both parts.

More generally it is appreciated that the manner in which the onset correction mandated by the SFT output (FIG. 1) is effected is determined by the MOPC output to modifier 14 (FIG. 1).

Similarly, following one or more patterns, the onsets of the BAS signal 200 and the stimulus input 210 may not coincide, as indicated at reference numeral 232, where the onset of the stimulus input leads the onset of the BAS signal by a time duration S2.

In order to compensate for this lead, the present invention causes the onset of a following stimulus input pattern, indicated by reference numeral 233 to be moved backward by an amount D2 which may be equal to S2 or be a suitably weighted amount dependent on S2, so as to reduce or eliminate the amount of lead, as indicated at reference numeral 235. The early onset is preferably achieved by decreasing the duration of the expiration influencing part of the stimulus signal or alternatively decreasing the duration of the inspiration influencing part or both parts.

It is appreciated that due to the various factors affecting the timing of the BAS signal at successive patterns, the BAS signal pattern onsets may lead or lag the stimulus input pattern onsets in a random or pseudorandom manner. The purpose of this feature of the present invention is to limit, insofar as possible, the time extent of such lead or lag, thereby to enhance the physiological effectiveness of the resulting entrainment.

Figure 9A:
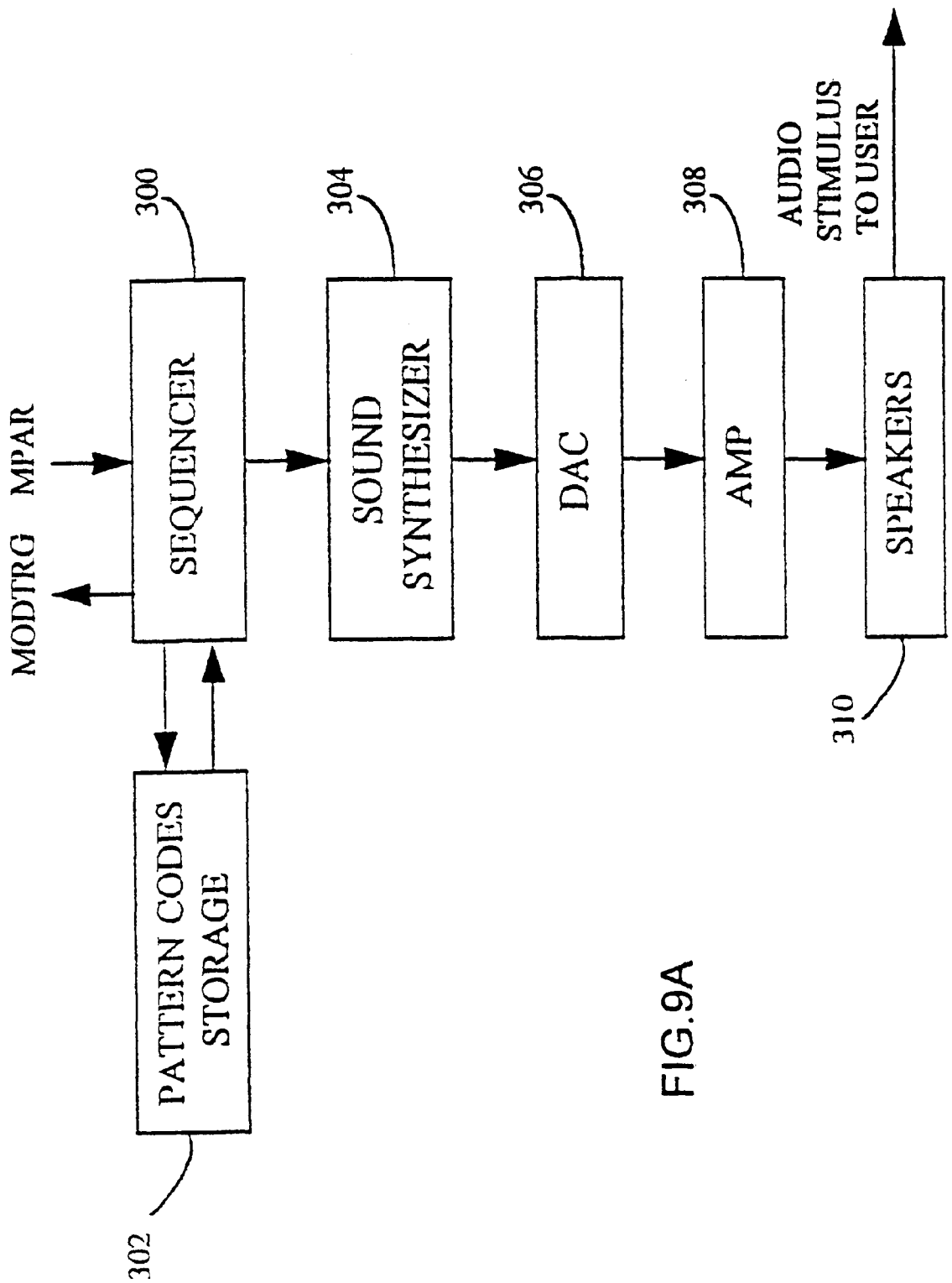
Figure 9B:
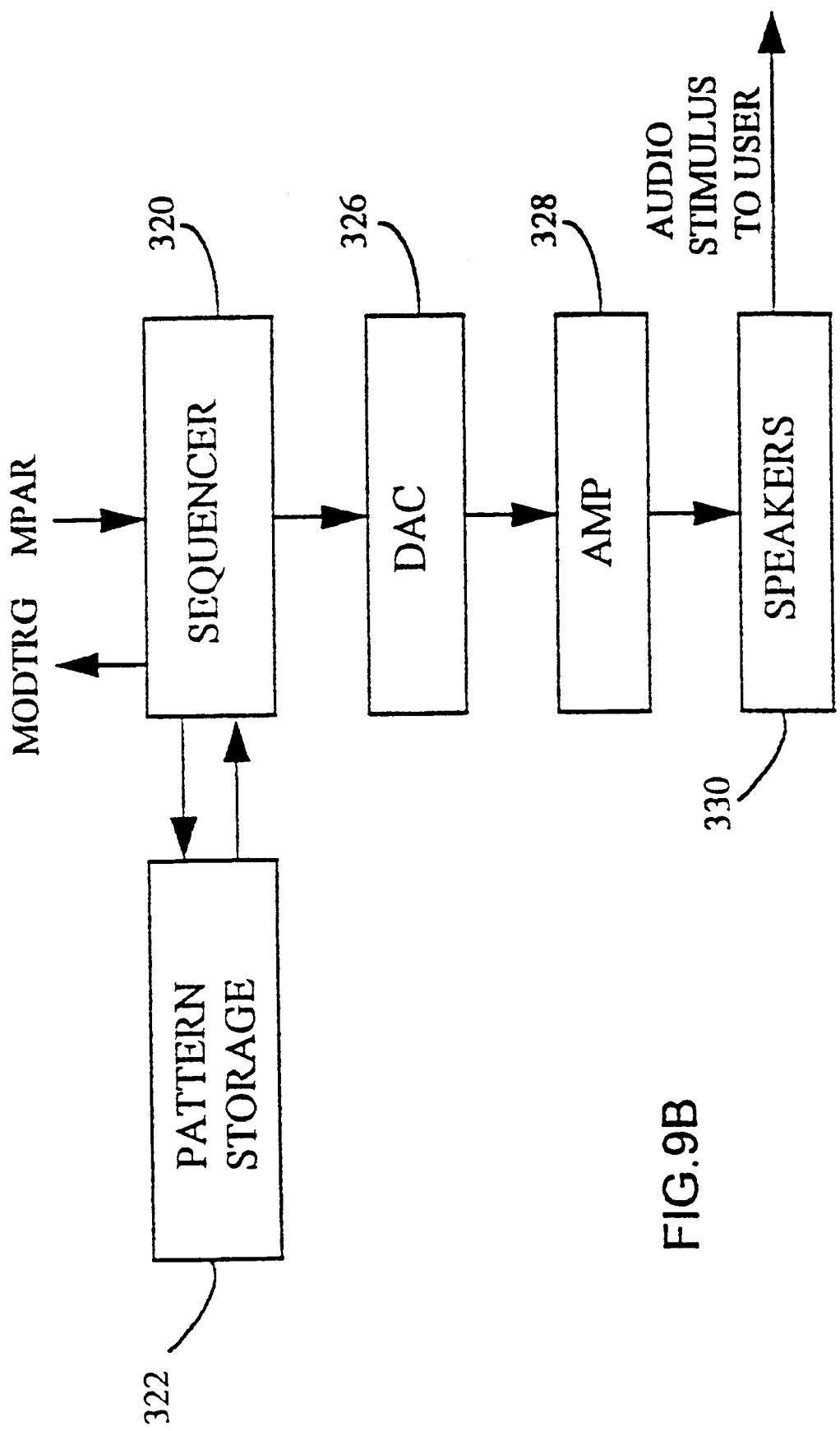

Reference is now made to FIGS. 9A, 9B & 9C, which are block diagrams illustrating the three alternative embodiments of the structure of a pattern generator employed in an audio stimulus generating version of the system of FIG. 1 whose operation is illustrated generally in FIG. 4.

Referring specifically to FIG. 9A, it is seen that the pattern generator is an audio pattern generator including a sequencer 300 which receives the MPAR output (FIG. 4). The sequencer 300 interfaces with a pattern codes storage device 302 which stores predetermined pattern codes which are employed to operate a sound synthesizer 304 in accordance with the timing and strategy established by the MPAR input. The sequencer 300 also provides the MODTRG output to shift detector 18 (FIG. 1).

The output of the sound synthesizer 304 is supplied via a digital to analog converter 306 and an amplifier 308 to audio output devices, such as speakers 310, which provide the stimulus input to the user (FIG. 1).

Referring now specifically to FIG. 9B, it is seen that the pattern generator is an audio pattern generator including a sequencer 320 which receives the MPAR output (FIG. 4). The sequencer 320 interfaces with a pattern storage device 322 which stores predetermined sound patterns, which are preferably randomly accessible digitally recorded sound segments and are outputted via the sequencer 320 in accordance with the timing and strategy established by the MPAR input. The sequencer 320 also provides the MODTRG output to shift detector 18 (FIG. 1).

The output of the pattern storage device 322 is supplied via a digital to analog converter 326 and an amplifier 328 to audio output devices, such as speakers 330, which provide the stimulus input to the user (FIG. 1).

Referring specifically to FIG. 9C, it is seen that the pattern generator is an audio pattern generator including a timing controller 350 which receives the MPAR output (FIG. 4). The timing controller 350 provides ON/OFF and select commands to a sound generator 352 in accordance with the timing and strategy established by the MPAR input. The timing controller 350 also provides the MODTRG output to shift detector 18 (FIG. 1).

The output of the sound generator 352 is supplied via an amplifier 358 to audio output devices, such as speakers 360, which provide the stimulus input to the user (FIG. 1).

Figure 10A:
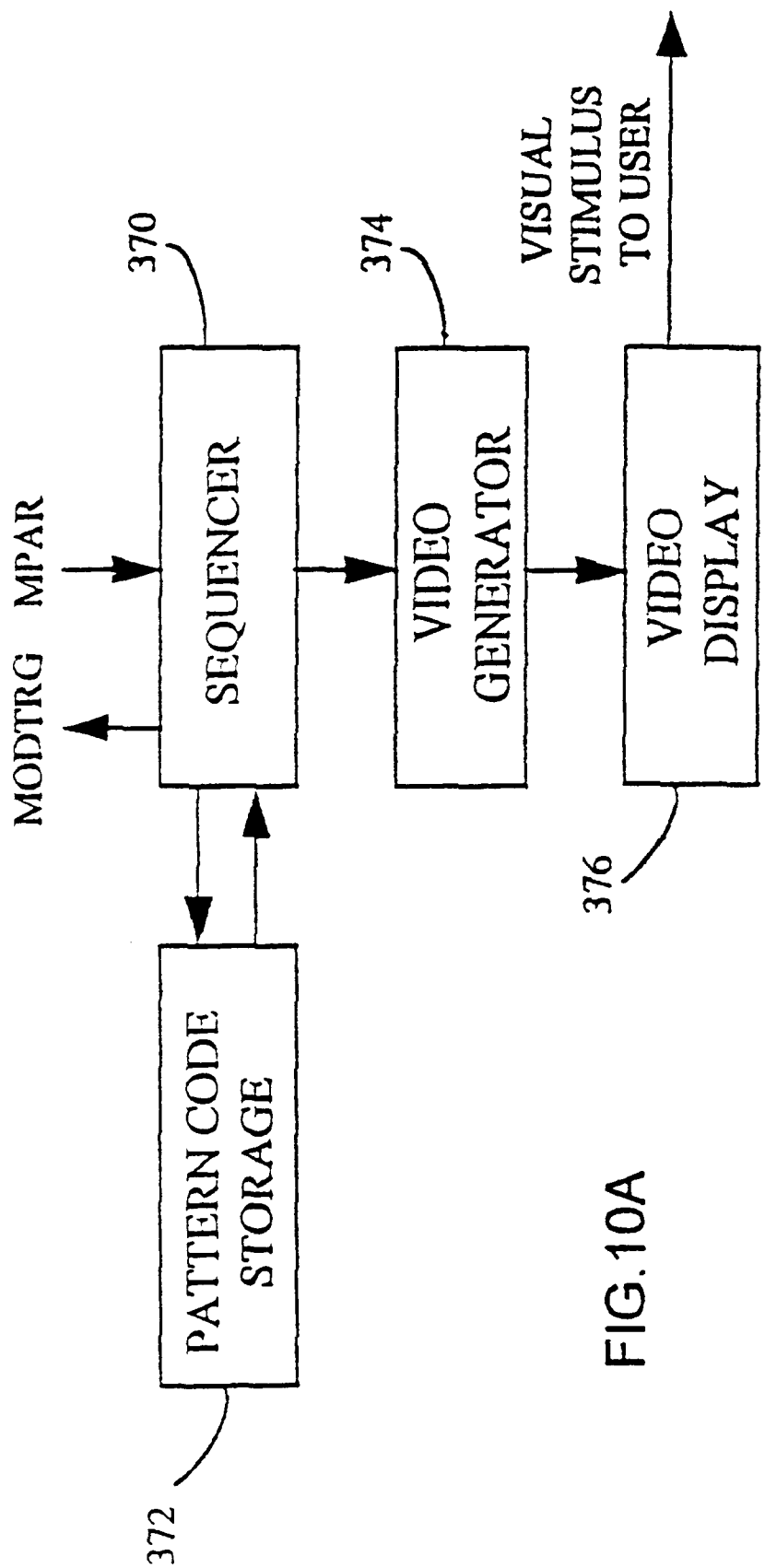
FIGS. 10A and 10B are block diagrams illustrating two alternative embodiments of the structure of a pattern generator employed in a visual stimulus generating version of the system of FIG. 1 whose operation is illustrated generally in FIG. 4.
Figure 10B:
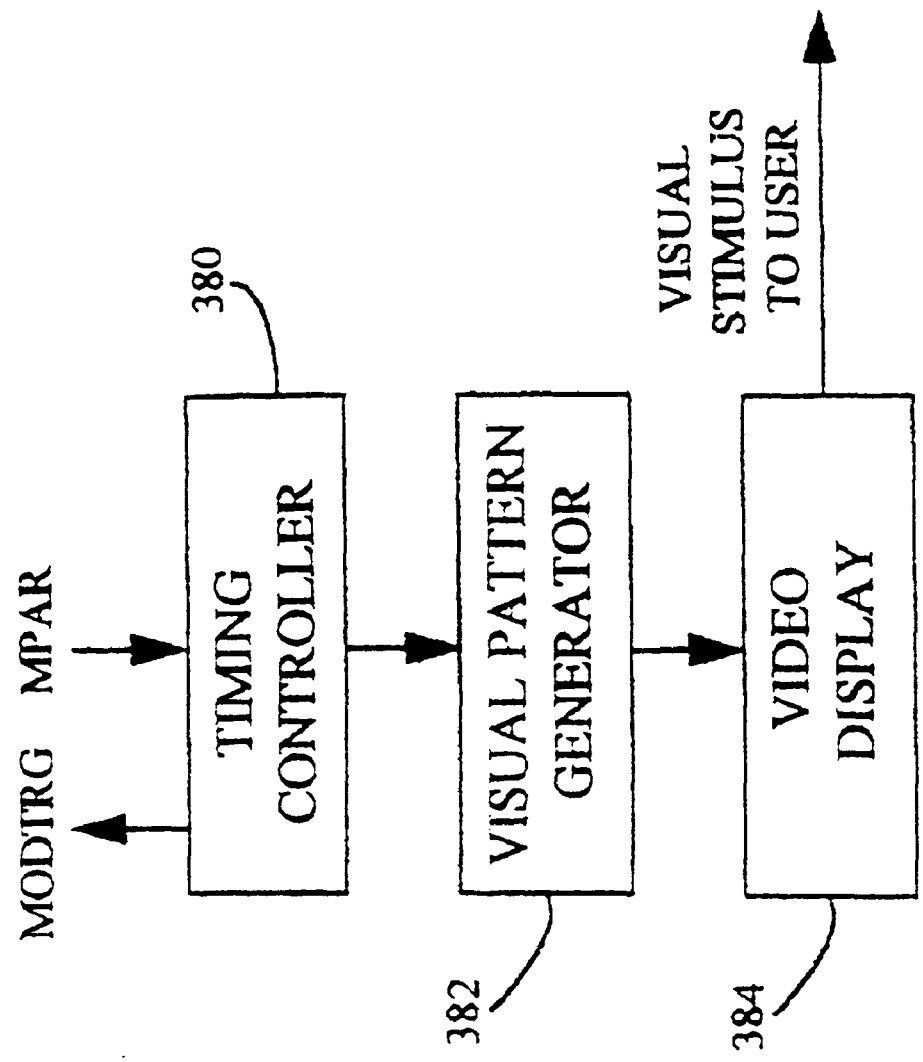

Reference is now made to FIGS. 10A and 10B, which are block diagrams illustrating two alternative embodiments of the structure of a pattern generator employed in a visual stimulus generating version of the system of FIG. 1.

Referring specifically to FIG. 10A, it is seen that the pattern generator is a visual pattern generator including a sequencer 370 which receives the MPAR output (FIG. 4) The sequencer 370 interfaces with a pattern codes storage device 372 which stores predetermined pattern codes which are employed to operate a video generator 374 in accordance with the timing and strategy established by the MPAR input. The sequencer 370 also provides the MODTRG output to shift detector 18 (FIG. 1).

The output of the video generator 374 is supplied to a video display 376, which provides the stimulus input to the user (FIG. 1).

Referring specifically to FIG. 10B, it is seen that the pattern generator is a visual pattern generator including a timing controller 380 which receives the MPAR input (FIG. 4). Timing controller 380 provides ON/OFF and select commands to a visual pattern generator 382 in accordance with the timing and strategy established by the MPAR input. The timing controller 380 also provides the MODTRG output to shift detector 18 (FIG. 1).

The output of the visual pattern generator 382 is supplied to a display 384, preferably an LCD display, which provides the stimulus input to the user (FIG. 1).

Figure 11A:
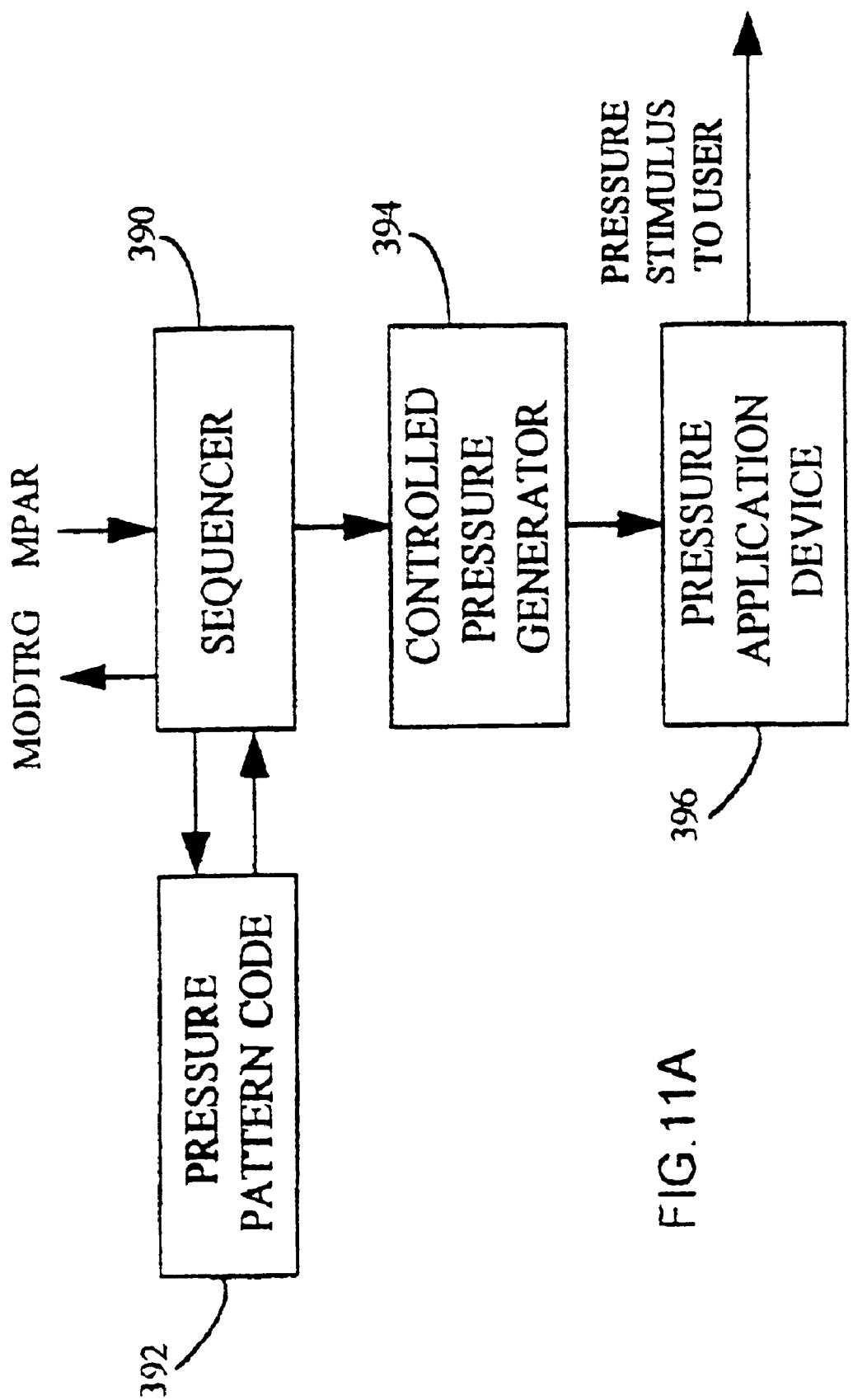

Reference is now made to FIG. 11A and 11B, which are block diagrams illustrating two alternative embodiments of a pattern generator employed in a pressure stimulus generating version of the system of FIG. 1.

Referring specifically to FIG. 11A, it is seen that the pattern generator is a pressure pattern generator including a sequencer 390 which receives the MPAR output (FIG. 4). The sequencer 390 interfaces with a pressure pattern codes storage device 392 which stores predetermined pressure pattern codes which are employed to operate a controlled pressure generator 394 in accordance with the timing and strategy established by the MPAR input. The sequencer 390 also provides the MODTRG output to shift detector 18 (FIG. 1).

The output of the controlled pressure generator 394 is supplied to a pressure application device 396, which provides the stimulus input to the user (FIG. 1).

Referring specifically to FIG. 11B, it is seen that the pattern generator is a pressure pattern generator including a timing controller 400 which receives the MPAR output (FIG. 4). Timing controller 400 provides ON/OFF and select commands to a controlled pressure generator 402 in accordance with the timing and strategy established by the MPAR input. The timing controller 400 also provides the MODTRG output to shift detector 18 (FIG. 1).

The output of the pressure pattern generator 402 is supplied to a pressure application device 404, preferably a cuff or other tactile output device, which provides the stimulus input to the user (FIG. 1).

Figure 12A:
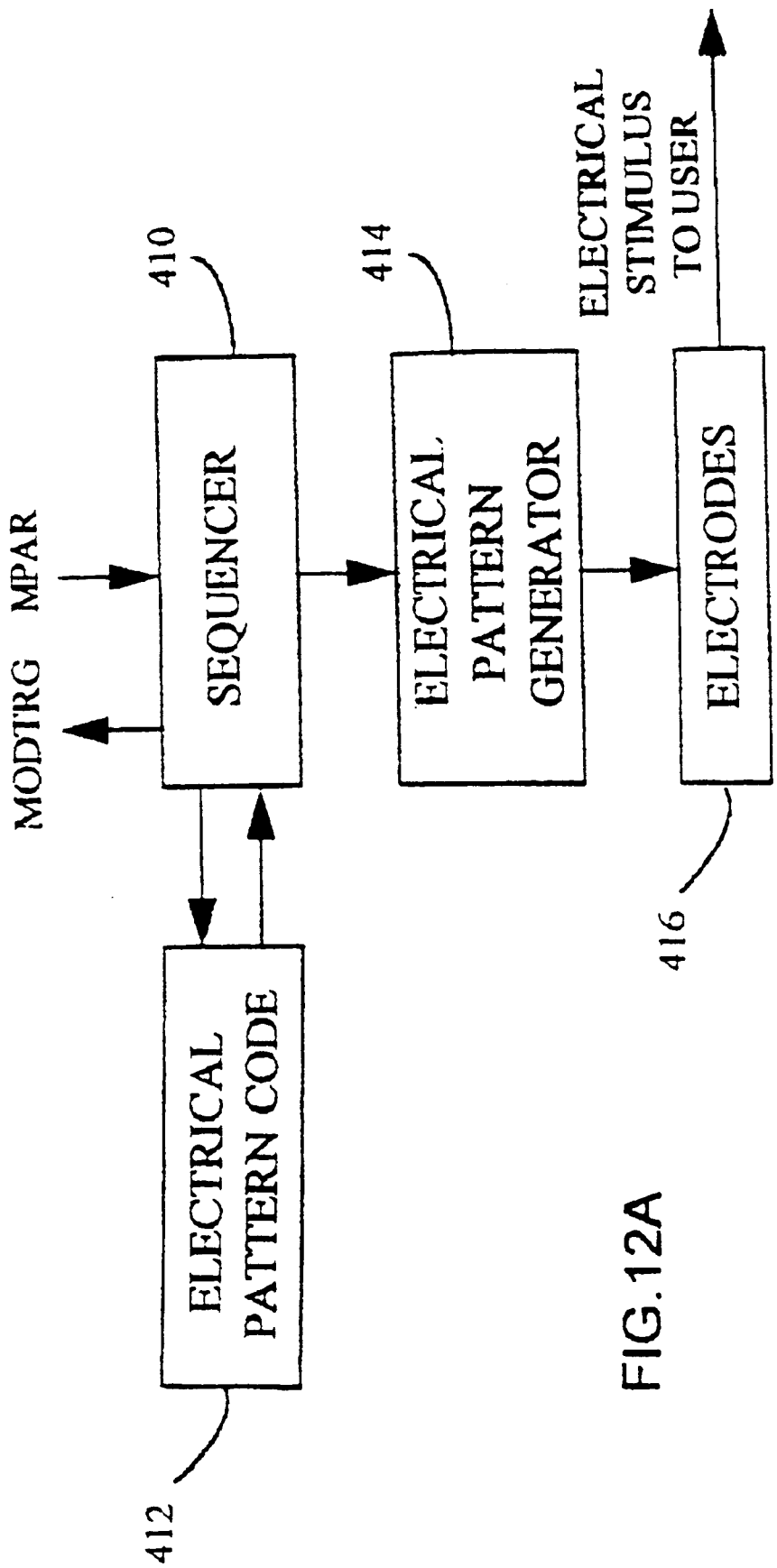
FIGS. 12A and 12B are block diagrams illustrating two alternative embodiments of a pattern generator employed in a electrical stimulus generating version of the system of FIG. 1 whose operation is illustrated generally in FIG. 4.
Figure 12B:
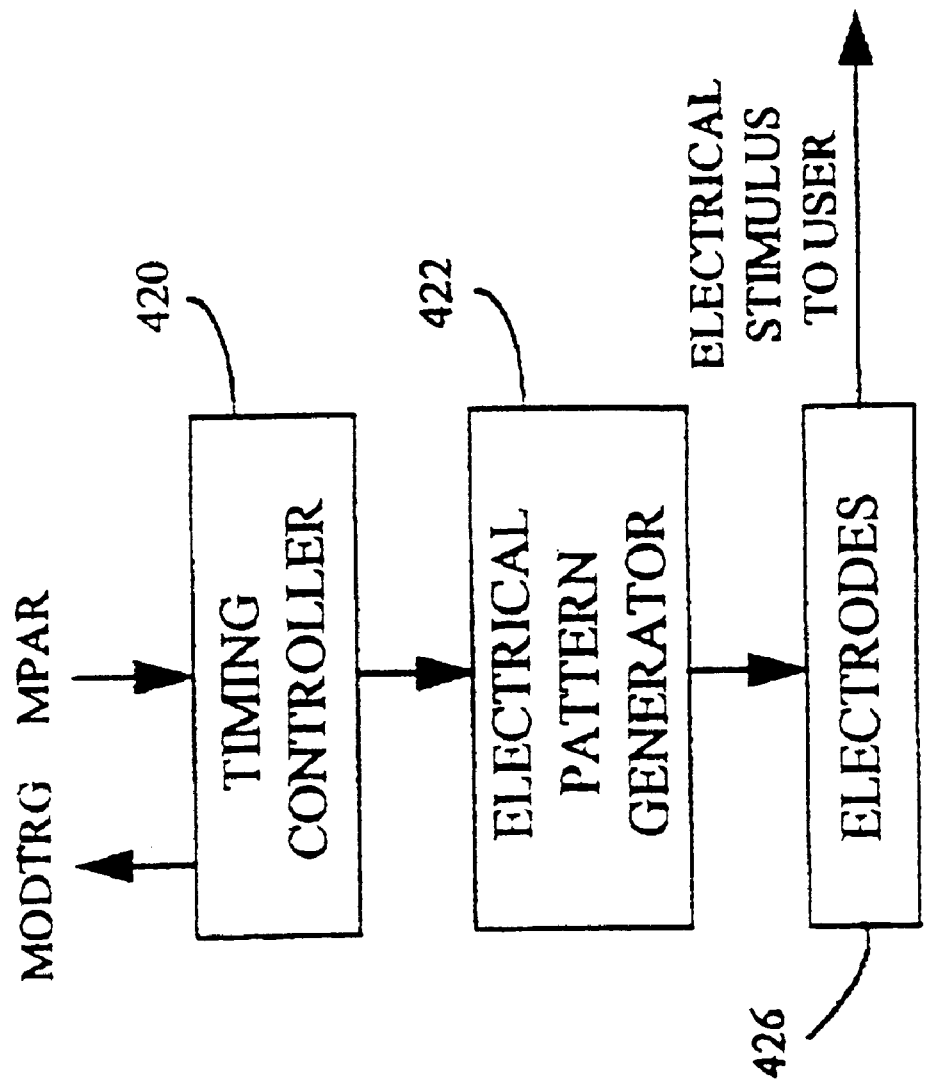

Reference is now made to FIGS. 12A and 12B, which are block diagrams illustrating two alternative embodiments of a pattern generator employed in a electrical stimulus generating version of the system of FIG. 1.

Referring specifically to FIG. 12A, it is seen that the pattern generator is an electrical pattern generator including a sequencer 410 which receives the MPAR output (FIG. 4). The sequencer 410 interfaces with an electric pattern codes storage device 412 which stores predetermined electrical pattern codes which are employed to operate a current pattern generator 414 in accordance with the timing and strategy established by the MPAR output. The sequencer 410 also provides the MODTRG output to shift detector 18 (FIG. 1).

The output of the current pattern generator 414 is supplied to an electric impulse application device, such as electrodes 416, which provide the stimulus input to the user (FIG. 1).

Referring specifically to FIG. 12B, it is seen that the pattern generator is an electrical pattern generator including a timing controller 420 which receives the MPAR input (FIG. 4). Timing controller 420 provides ON/OFF and select commands to a current pattern generator 422 in accordance with the timing and strategy established by the MPAR input. The timing controller 420 also provides the MODTRG output to shift detector 18 (FIG. 1).

The output of the electrical pattern generator 422 is supplied to an electric impulse application device, such as electrodes 426, which provide the stimulus input to the user (FIG. 1).

Figure 13:
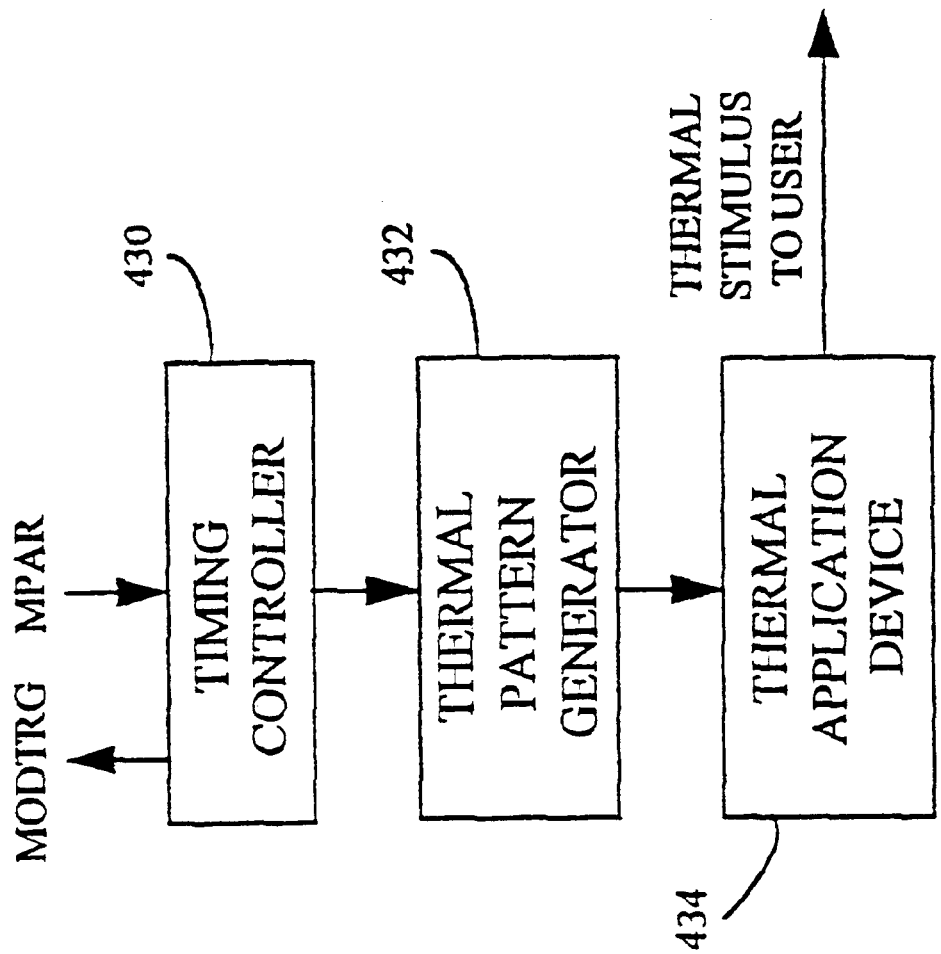
FIG. 13 is a block diagram illustrating an embodiment of a pattern generator employed in a thermal stimulus generating version in the system of FIG. 1 whose operation is illustrated generally in FIG. 4.

Reference is now made to FIG. 13, which is a block diagram illustrating an embodiment of a pattern generator employed in a thermal stimulus generating version in the system of FIG. 1. It is seen that the pattern generator is a thermal pattern generator including a timing controller 430 which receives the MPAR input (FIG. 4). Timing controller 430 provides ON/OFF and select commands to a thermal pattern generator 432 in accordance with the timing and strategy established by the MPAR input. The timing controller 430 also provides the MODTRG output to shift detector 18 (FIG. 1).

The output of the thermal pattern generator 432 is supplied to an thermal application device 434, such as a heating pad, which provide the stimulus input to the user (FIG. 1).

Figure 14:
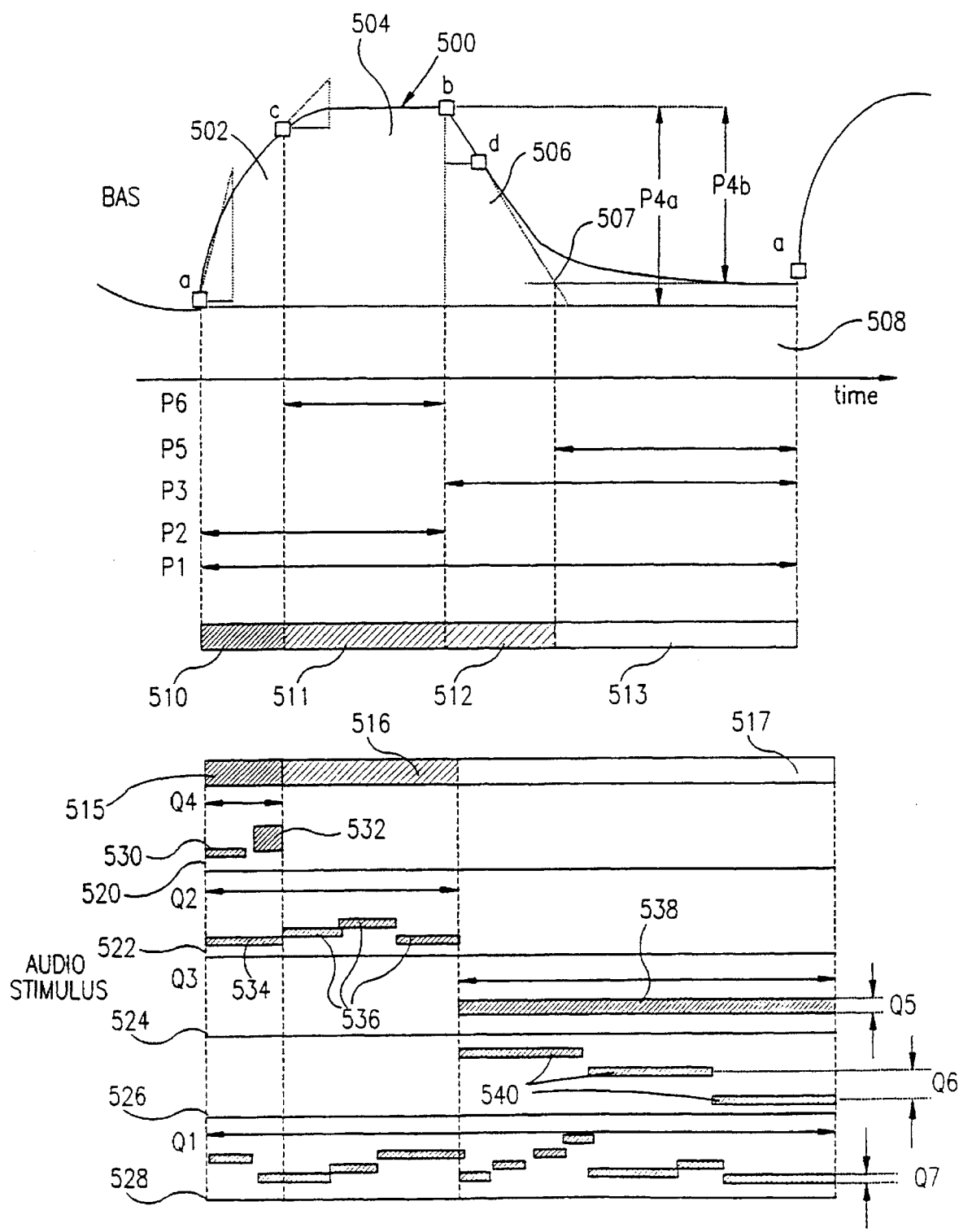
FIG. 14 is an illustration of a typical respiration signal and modification of the respiration signal through the use of an audio stimulus in accordance with a preferred embodiment of the present invention.

Reference is now made to FIG. 14 which is an illustration of a typical respiration signal and modification of the respiration signal through the use of an audio stimulus in accordance with a preferred embodiment of the present invention.

The respiration signal, indicated by reference numeral 500, is similar to that shown in FIG. 6 but includes additional features which are subject to the above-described analysis of special points. The modification of the respiration signal by using an audio stimulus shown in FIG. 14 may be similar to that of FIG. 7, but employs more complex relationships between PAR signals, which represent the moving averages of the raw parameters of the analyzed biorhythmic activity signal BAS, and the MPAR signals, which represent the modified parameters which control the audio stimulus input to the user.

Typical special points which characterize an nth recurrent pattern in the BAS signal 500 include the following:

a—the location where the first time derivative has a maximum following a local minimum;

b—the location at which the BAS signal reaches a maximum, the first time derivative is equal to zero and the second time derivative is negative;

c—the location at which the first time derivative crosses the value of a predetermined fraction, e.g. 0.2 of the value of the first time derivative at point a;

d—the location at which the amplitude of the BAS signal crosses the value of a predetermined fraction, e.g. 0.7 of the signal amplitude at point b, calculated with reference to point a.

Throughout the present specification and claims, point a, is taken to represent the onset of the BAS signal.

The special points a–d for each pattern n are stored and the following raw parameters are calculated therefrom:

P1(n) Pattern duration—the duration of pattern n, which is the sum of P2(n) and P3(n) defined hereinbelow;

P2(n) Pattern rise time—the time separation between point a and the following point b, n indicating the number of the pattern;

P3(n) Pattern fall time—the time separation between point b and following point a, n indicating the number of the pattern;

P4a(n) Inspiration amplitude—the signal amplitude at point b measured with reference to previous point a;

P4b(n) Expiration amplitude—the signal amplitude at point b measured with reference to following point a;

P5(n) Pattern rest time—the time separation between point a of pattern n+1 and a point 507 obtained by crossing a line connecting points b and d in pattern n and a horizontal line passing through point a of pattern n+1. P5(n) is calculated in practice based inter alia on parameters P4a(n) and P4b(n).

P6(n) Breath holding time—the time separation between points c and b.

Referring to the above special points it may be appreciated that the BAS pattern 500 is composed of four parts, an inspiration part 502, which is the rising part of the BAS signal and corresponds to active inspiratory efforts of a user, a breath holding part 504, which is the relatively flat part of the signal and corresponds to the inflated state of the user's lungs of the user, which is controlled voluntarily by the user in Yoga exercises; an expiration part 506, which is part of the falling part of the BAS signal and corresponds to the recoil of the user's chest back to its relaxed state; and a rest part 508, which is the rest of the falling part and represents a static effortless state of the respiratory cycle known as "post expiration". The rest part 508 is known to be sensitive to mental stress or relaxation of the user.

The durations of the various parts of the BAS pattern are represented graphically by differently shaded parts of the diagram and are indicated by reference numerals as follows Inspiration part—510

Breath holding part—511

Expiration part—512

Rest part—513

The lower part of FIG. 14 includes an example of a three-part audio stimulus, which constitutes the input to the user and is produced by the audio pattern generator shown in FIG. 9A, which is controlled by the modified parameters MPAR in response to modified operator commands MOPC supplied by driver 16 (FIG. 1) in response to operator selection.

In this example, the selected driving strategy is to induce elongation of the duration 511 of the breath holding part 504 and elongation of the falling part which includes durations 512 and 513 of the expiration part 506 and the rest part 508 respectively of the BAS signal of the user. The selected driving strategy also calls for increasing the ratio between the duration 513 of the rest part 508 to the duration 512 of the expiration part 506. At the same time, the attention of the user to the music is preferably maintained by adding non-recurrent components to the audio stimulus. Randomness can be applied to both the structure of the music and the duration of specific parts of the music. Altogether, the structure of the audio stimulus is designed to increase the entrainment efficiency, while at the same time entertaining the user. It is to be appreciated that for the sake of conciseness and clarity, the features of shift correction, described hereinabove with reference to FIG. 8, are not here described with reference to FIG. 14, although they are employed in practice.

In accordance with a preferred embodiment of the present invention an audio stimulus pattern is provided including an inspiration part whose duration is indicated by reference numeral 515, a breath holding part, whose duration is indicated by reference numeral 516 and a falling part, whose duration is indicated by reference numeral 517.

The audio stimulus pattern is shown in the illustrated example of FIG. 14 as including five outputs 520, 522, 524, 526 and 528, each may be corresponding to a different musical instrument. Each output appears along a separate track and is designated as follows: The height of the output indication along each track indicates the pitch thereof, while the thickness of the output indication indicates its intensity.

Output 520 is seen to comprise two successive tones 530 and 532, having equal duration, tone 530 having a pitch and an intensity lower than that of tone 532. The overall duration 515 of tones 530 and 532 is designated as MPAR Q4 and is equal to the moving average of raw parameter P2 minus the moving average of raw parameter P6, here designated <P2>–<P6>, which is equal to the current average inspiration duration of the user.

Output 522 is seen to comprise a single recurring tone 534 having a duration 515 designated as MPAR Q4 and a plurality of non-recurring tones 536, collectively having a duration 516, corresponding in time mainly to the breath holding part 504 of the BAS signal. The overall duration of output 522 is designated as MPAR Q2 and is typically equal to 1.05–1.1 times the moving average of raw parameter P2, here designated <P2>, and is 5% to 10% longer than the current average inspiration duration of the user.

Output 524 is seen to comprise a single recurring tone 538 having a variable duration 517 designated as MPAR Q3, corresponding in time mainly to the falling part 506 & 508 of the BAS signal. Duration 517 (MPAR Q3) is preferably equal to the moving average of raw parameter P3 plus one-half a second plus a random time factor R, where R is between –0.25 seconds and +0.25 seconds, here designated <P3>+0.5+R. The intensity of output 524 is designated as MPAR Q5 and is proportional to the ratio of the average rest time to the average expiration time in the BAS signal. This ratio is expressed as <P3>/(<P3>–<P5>).

Output 526 is seen to comprise a plurality 540 of tones separated from each other in pitch by equal pitch separations, designated as MPAR Q6. These pitch separations are proportional to the reciprocal of the moving average of the pattern duration, expressed by 1/<P1>.

The duration of the individual ones of the plurality 540 of tones are selected to be about one second. The overall duration of the plurality 540 of tones is designated by MPAR Q3, referred to above.

Output 528 is seen to comprise a generally non-recurring series of tones of varying number and duration, whose intensity designated as MPAR Q7, which is proportional to the moving average amplitude of raw parameter P4a, expressed by <P4a>. Output 528 is provided only when MPAR Q1, which equals the sum of Q2 and Q3, is equal to the moving average of the pattern duration, i.e. <P1>, is greater than a given value, typically 6 seconds.

In general, all or some of the series of tones, designated as outputs 520, 522, 525 and 528, which are presented as discrete tones, may be replaced by continuous or partially continuous pitch variations.

Figure 15:
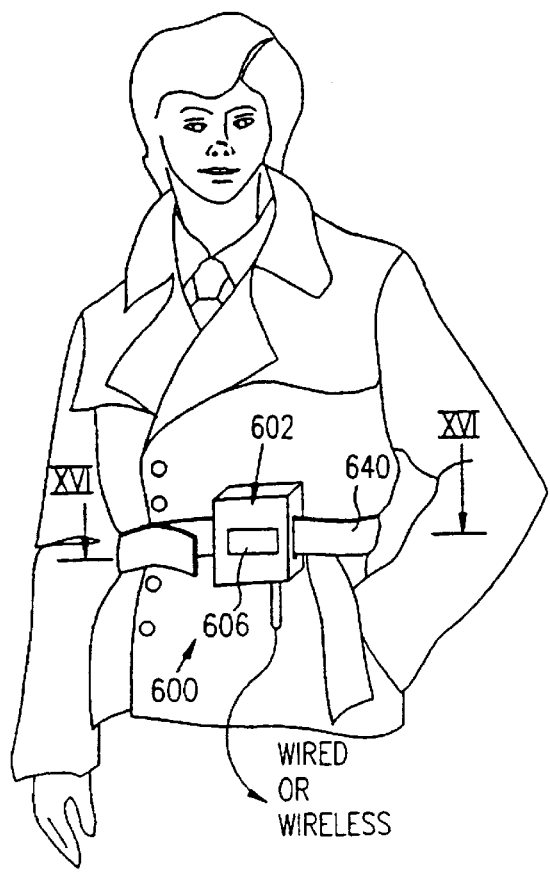
FIG. 15 is a simplified illustration of a biorhythmic activity monitoring device and biorhythmic activity sensor, constructed and operative in accordance with a preferred embodiment of the present invention.
Figure 16A:
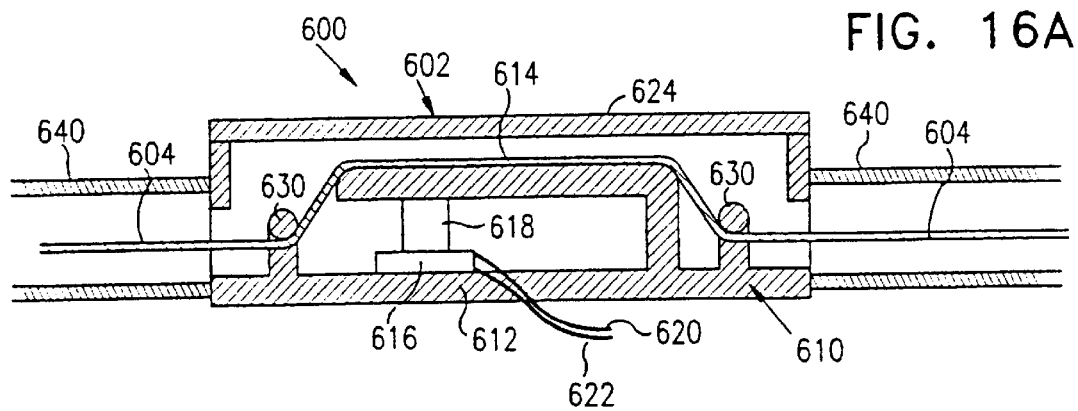
FIG. 16A is a simplified sectional illustration of a portion of the biorhythmic activity sensor of FIG. 15, taken along lines XVI—XVI in FIG. 15, and including a force transducer which responds to compressive stress.
Figure 16B:
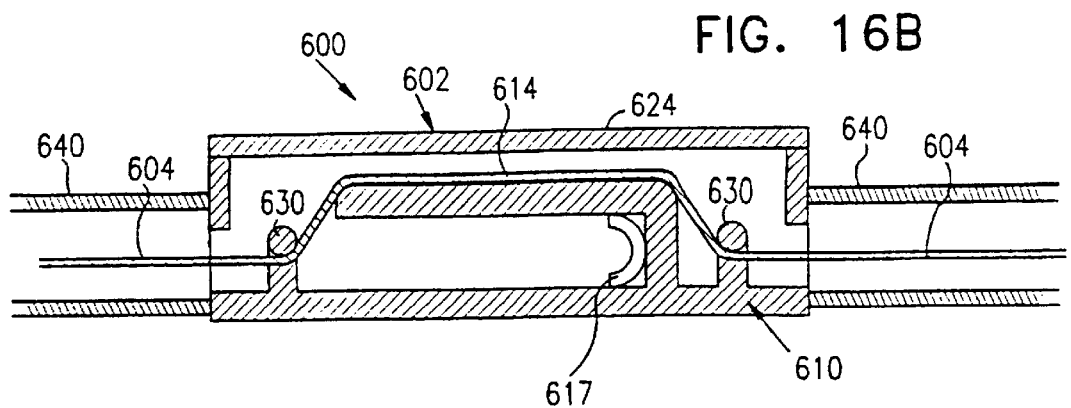
FIG. 16B is a simplified sectional illustration of a portion of the biorhythmic activity sensor of FIG. 15, taken along lines XVI—XVI in FIG. 15, and including a force transducer which responds to stretching.

Reference is now made to FIGS. 15, 16A and 16B which illustrate a biorhythmic activity monitoring device 600, constructed and operative in accordance with a preferred embodiment of the present invention. Biorhythmic activity monitoring device 600 may be employed with monitor 10 of the system of FIG. 1 disclosed hereinabove.

Stress detecting device 600 preferably includes a biorhythmic activity sensor 602 slidably disposed on a belt 604 worn by a user. Belt 604 is preferably elastic and/or stretchable along at least a portion of its length. Output signals of sensor 602 may be preferably transferred to monitoring apparatus (not shown) either by wired or wireless communication. Alternatively, device 600 may be provided with a display 606 for displaying information obtained from the output of sensor 602 by appropriate processing.

As seen best in FIG. 16A, sensor 602 preferably comprises a deformable structure 610 having a U-shaped structure and constructed of an elastic material so as to permit angular deformation between a pair of legs 612 and 614 of the U-shaped structure. A force transducer 616 is preferably fixedly attached to an inner surface of leg 612, such as by bonding thereto, and is mechanically linked via an elastic body member 618 to an inner surface of leg 614.

Alternatively, as seen in FIG. 16B, force transducer 616 together with elastic body member 618, which respond to compressive stress only, may be replaced by a force transducer 617 which responds to stretching and may be located in any part of deformable structure 610 that deforms under forces exerted by belt 604 thereupon. Force transducer 616 or 617 may be responsive to an electrical property, such as resistance, capacitance or inductance, in which case two electric leads 620 and 622 may be attached thereto for transmitting electrical output thereof. It is appreciated that deformable structure 610 may be fabricated in a variety of other shapes, as long as a deformation of the structure 610 may be transferred to transducer 616.

Deformable structure 610 of sensor 602 presses against a user's body or clothing by stretchable belt 604. Displacement of belt 604 in a direction generally perpendicular to its length is preferably limited by a cover 624 or any other suitable device, such as a flange (not shown) on deformable structure 610. An upper surface of leg 614 is preferably smooth and cover 624 is configured so as not to touch belt 604 and to permit sensor 602 to slide along belt 604.

Circumferential changes of a user's body, such as at the chest or abdomen, cause corresponding length changes in elastic belt 604 which can be monitored by sensor 602. These length changes cause tension changes in belt 604 which cause deformation of deformable structure 610, since belt 604 abuts thereagainst. Transducer 616 then outputs a signal in correspondence with a deformation of deformable structure 610. The structure of sensor 602 eliminates force components in belt 604 not associated with the circumferential changes. This feature makes sensor 602 relatively insensitive to body movements not associated with breathing.

The sensor disclosed in U.S. Pat. No. 5,423,328 is also capable of monitoring breathing of a user, as described therein. However, the sensor of U.S. Pat. No. 5,423,328 suffers from two problems which the present invention solves, as described hereinbelow.

The first problem is that the force acting on the base of the '328 sensor depends on the angle between the elastic belt and the top of the sensor base. This means that the '328 sensor is sensitive to the particular position of the sensor on the user's body. For example, the '328 sensor will give a different output depending upon whether it is mounted on the abdomen or on the breast of a woman, which differ in curvature. The '328 sensor does not function if mounted over a concave surface, such as between a woman's breasts or folds of abdomen in fat persons, and also does not function when a user is lying on the sensor base, so the sensor is "buried". This is because the sensor base of the '328 sensor is not supported, and no force is transferred in these cases to the transducer.

The second problem is that the '328 sensor is sensitive to "belt trapping". If a user leans against a surface in such a way that the belt is sandwiched between the user's body and the supporting surface, e.g., while sleeping or leaning back against a chair, the belt becomes trapped with the result that changes in the chest or abdomen circumference at this region do not induce corresponding variations in the belt length.

The present invention solves the first problem of angle dependence by providing a pair of smooth cylindrical guides 630 on an extension of leg 612 of deformable structure 610, through which elastic belt 604 is guided. As a result, tensions in belt 604 are transferred to leg 614 of deformable structure 610 at a constant angle, irrespective of the angle at which elastic belt 604 reaches deformable structure 610. In addition, the support of leg 612 by a body surface does not play any role in the function of device 600.

Reference is now made additionally to FIGS. 17A, 17B and 17C. The present invention solves the second problem of "belt trapping" by providing a belt protector 640 that creates a low-friction guide for elastic belt 604 which runs therethrough. Because of the low coefficient of friction between belt 604 and belt protector 640, belt 604 is free to expand along its length without being "trapped" against or "pinched" between internal parts of belt protector 640.

Belt protector 640 is preferably flexible, at least along a portion of its length. Belt protector 640 may be constructed from one or more parts, each of which may be elastic or flexible. Belt protector 640 may have a variety of forms. FIG. 17A illustrates a generally rectangular cross section. FIG. 17B illustrates a generally circular cross section, and FIG. 17C illustrates a generally spiral form. Preferably, one portion of belt protector 640 may be attached to another portion thereof, so as to facilitate wrapping of belt protector 640 around a user. For example, at least a portion of an outer surface of belt protector 640 may be constructed of VELCRO brand multiple hook fastener so as to self-stick to another portion of the outer surface. Alternatively, especially for the circular cross section configuration shown in FIG. 17B, belt protector 640 may include a silicone rubber tube which may be caused to adhere to another portion of belt protector 640.

It is noted that device 600 may be provided with guides 630 but without belt protector 640, or vice versa, without guides 630 but with belt protector 640, depending on the particular requirements and implementation of device 600. Guides 630 may be suitable adapted to the configuration of belt protector 640. For example, in the case of a circular cross sectional belt 604 and belt protector 640, guides 630 may include a hole or grooves for guiding therethrough belt 604.

The structure of sensor 602 enables calibrating sensor output with respect to magnitude of breathing movements. It is essential for signal calibration of sensor 602 that circumferential changes associated with breathing movements of a user should be translated into proportional changes in the length of belt 604, independently of the chest/abdomen diameter. This may be accomplished simply by wrapping belt 604 completely around the user's body, as shown in FIG. 15. It is appreciated that monitoring circumferential changes, as disclosed, is not restricted to breathing movements. For example, uterus contractions produce circumferential changes at the belly height in pregnant women. Quantification of such contractions, without exerting significant pressure, is a feature with significant commercial importance.

The following discussion will show that this arrangement meets the above mentioned requirement.

Let L be the length of the stretchable part of belt 604, which subtends an angle $\phi$ (360° per turn), when it is wrapped around. The relation $L=k\phi$, is preserved for a constant k, if the belt sticks to the body, k being a geometrical proportionality constant. Thus, the same relation holds for circumferential changes, i.e. $\Delta L=k\Delta\phi$. Thus $\Delta L/L=\Delta\phi/\phi$, as required.

In the embodiments of FIGS. 15, 16A and 16B, belt protector 640 is preferably attached to sensor 602. Reference is now made to FIG. 18 which illustrates a portion of a biorhythmic activity sensor 650, constructed and operative in accordance with another preferred embodiment of the present invention. In this embodiment, deformable structure 610 is encapsulated by belt protector 640, and cover 624 may be eliminated if desired. Deformable structure 610 is preferably fixedly attached to one side of belt protector 640. One of the smooth cylindrical guides 630 may be eliminated, and instead, belt 604 is preferably fixed to a post 651.

Reference is now made to FIG. 19 which illustrates a portion of a biorhythmic activity sensor 660, constructed and operative in accordance with yet another preferred embodiment of the present invention.

Biorhythmic activity sensor 660 preferably includes a belt 662 which is disposed in a belt protector 664, which are preferably substantially identical to belt 604 and belt protector 640, respectively, described hereinabove. One end 666 of belt 662 is preferably fixed to an inner surface of belt protector 664, and an opposite end 668 of belt 662 is preferably attached to a force transducer 670. Force transducer 670 responds to stretching forces acting thereupon, and may be electrical, in which case, it is supplied with two electrical leads 672 and 674. This embodiment thus eliminates the need for a deformable structure and belt guides of the embodiments of FIGS. 15–18.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the present invention is defined only by the claims which follow:

What is claimed is:

1. A system for modifying naturally occurring biorhythmic activity comprising:

a monitor for analyzing biorhythmic activity of a user;

a biorhythmic activity modifier for providing to the user a stimulus input which is operative to change at least one aspect of the biorhythmic activity of the user;

a driver operative to control the operation of the biorhythmic activity modifier, so as to change at least one non-frequency characteristic of the input to the user, in response to changes in the biorhythmic activity of the user during operation of the modifier;

and wherein said monitor comprises:

an elastic belt stretchable along a longitudinal length thereof and which may be wrapped around at least a portion of a body of the user, which portion undergoes circumferential changes as a result of the biorhythmic activity of the user;

a deformable structure against which abuts at least a portion of said belt, wherein said belt when stretched applies a force against and deforms said deformable structure;

a force transducer in contact with said deformable structure which outputs a signal in correspondence with a deformation of said deformable structure; and a plurality of guides attached to said deformable structure, through which said belt is guided, such that tensile forces in said belt are transferred to a portion of said deformable structure at a constant angle, irrespective of an angle at which said belt reaches said deformable structure.

2. A system for modifying naturally occurring biorhythmic activity comprising:

a monitor for analyzing biorhythmic activity of a user;

a biorhythmic activity modifier for providing to the user a stimulus input which is operative to change at least one aspect of the biorhythmic activity of the user;

a driver operative to control the operation of the biorhythmic activity modifier, so as to change at least one non-frequency characteristic of the input to the user, in response to changes in the biorhythmic activity of the user during operation of the modifier;

and wherein said monitor comprises;

a belt protector;

a force transducer disposed in said belt protector; and an elastic belt stretchable along a longitudinal length thereof and which may be wrapped around at least a portion of a body of the user, which portion undergoes circumferential changes as a result of the biorhythmic activity of the user, said belt being disposed in said belt protector, one end of said belt being attached to an inner surface of said belt protector and an opposite end of said belt being attached to said force transducer, wherein said belt when stretched applies a force against said force transducer, thereby causing said force transducer to output a signal in correspondence with said force.

3. A system for modifying naturally occurring biorhythmic activity comprising:

a monitor for analyzing biorhythmic activity of a user;

a biorhythmic activity modifier for providing to the user a stimulus input which is operative to change at least one aspect of the biorhythmic activity of the user;

a driver operative to control the operation of the biorhythmic activity modifier, so as to change at least one non-frequency characteristic of the input to the user, in response to changes in the biorhythmic activity of the user during operation of the modifier;

and wherein said monitor comprises:

an elastic belt stretchable along a longitudinal length thereof and which may be wrapped around at least a portion of a body of the user, which portion undergoes circumferential changes as a result of the biorhythmic activity of the user;

a deformable structure against which abuts at least a portion of said belt, wherein said belt when stretched applies a force against and deforms said deformable structure;

a transducer in contact with said deformable structure which outputs a signal in correspondence with a deformation of said deformable structure; and a belt protector with a substantially low-friction inner surface through which is disposed said elastic belt.

4. A biorhythmic activity monitoring device comprising:

an elastic belt stretchable along a longitudinal length thereof and which may be wrapped around at least a portion of a body of a user, which portion undergoes circumferential changes as a result of a biorhythmic activity of the user;

a deformable structure against which abuts at least a portion of said belt, wherein said belt when stretched applies a force against and deforms said deformable structure;

a transducer in contact with said deformable structure which outputs a signal in correspondence with a deformation of said deformable structure; and a plurality of guides attached to said deformable structure, through which said belt is guided, such that tensile forces in said belt are transferred to a portion of said deformable structure at a constant angle, irrespective of an angle at which said belt reaches said deformable structure.

5. A biorhythmic activity monitoring device comprising:

a belt protector;

a force transducer disposed in said belt protector; and an elastic belt stretchable along a longitudinal length thereof and which may be wrapped around at least a portion of a body of a user, which portion undergoes circumferential changes as a result of a biorhythmic activity of the user, said belt being disposed in said belt protector, one end of said belt being attached to an inner surface of said belt protector and an opposite end of said belt being attached to said force transducer, wherein said belt when stretched applies a force against said force transducer, thereby causing said force transducer to output a signal in correspondence with said force.

6. A device according to claim 5 wherein said belt protector is flexible at least along a portion of its length.

7. A device according to claim 5 wherein said belt protector comprises a plurality of flexible parts.

8. A device according to claim 5 wherein said belt protector has a generally rectangular cross section.

9. A device according to claim 5 wherein said belt protector has a generally circular cross section.

10. A device according to claim 5 wherein said belt protector has a generally spiral form.

11. A device according to claim 5 wherein one portion of said belt protector is attachable to another portion thereof.

12. A biorhythmic activity monitoring device comprising:

an elastic belt stretchable along a longitudinal length thereof and which may be wrapped around at least a portion of a body of a user, which portion undergoes circumferential changes as a result of a biorhythmic activity of the user;

a deformable structure against which abuts at least a portion of said belt, wherein said belt when stretched applies a force against and deforms said deformable structure;

a transducer in contact with said deformable structure which outputs a signal in correspondence with a deformation of said deformable structure; and a belt protector with a substantially low-friction inner surface through which is disposed said elastic belt.

13. A device according to claim 12, wherein said belt protector is flexible at least along a portion of its length.

14. A device according to claim 12, wherein said belt protector comprises a plurality of flexible parts.

15. A device according to claim 12, wherein said belt protector has a generally rectangular cross section.

16. A device according to claim 12, wherein said belt protector has a generally circular cross section.

17. A device according to claim 12, wherein said belt protector has a generally spiral form.

18. A device according to claim 12, wherein one portion of said belt protector is attachable to another portion thereof.

* * * * *